US012806422B2

(12) United States Patent
Steinke et al.

(10) Patent No.: US 12,806,422 B2
(45) Date of Patent: Nov. 24, 2026

(54) USING STIMULATION CIRCUITRY TO PROVIDE DC OFFSET COMPENSATION AT INPUTS TO SENSE AMP CIRCUITRY IN A STIMULATOR DEVICE

(71) Applicant: Boston Scientific Neuromodulation Corporation, Valencia, CA (US)

(72) Inventors: G. Karl Steinke, Valencia, CA (US); Vahagn Hokhikyan, Northridge, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 286 days.

(21) Appl. No.: 18/450,148

(22) Filed: Aug. 15, 2023

(65) Prior Publication Data

US 2024/0058611 A1 Feb. 22, 2024

Related U.S. Application Data

(60) Provisional application No. 63/371,705, filed on Aug. 17, 2022.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/0551* (2013.01)

(58) Field of Classification Search
CPC .............. A61N 1/36139; A61N 1/0534; A61N 1/0551; A61N 1/36062; A61N 1/36125; A61B 5/24
See application file for complete search history.

(56) References Cited

U.S. PATENT DOCUMENTS 4,677,986 A 7/1987 Decote, Jr.
5,697,958 A 12/1997 Paul et al.
(Continued)

FOREIGN PATENT DOCUMENTS

EP 1147784 10/2001
WO 2015/077362 5/2015
(Continued)

OTHER PUBLICATIONS

International Search Report and Written Opinion regarding corresponding PCT Application No. PCT/US2023/072236, mailed Nov. 23, 2023.

*Primary Examiner* — Tammie K Marlen
*Assistant Examiner* — Maria Catherine Anthony
(74) *Attorney, Agent, or Firm* — Lewis & Reese, PLLC

(57) ABSTRACT

Techniques and circuitry are disclosed that provide DC offset compensation to equate the DC values of the inputs to sense amp circuitry used to sense neural responses in a stimulator device. When a DC offset is present at the inputs to the sense amp circuitry, the stimulation circuitry is used to remove this DC offset by providing one or more charge imbalanced pulses that are either net cathodic or net anodic. Control of the stimulation circuitry can occur using a DC offset compensation algorithm programmed into control circuitry of the stimulator device. Use of the stimulation circuitry itself to provide DC offset compensation is beneficial because it is already present in the stimulator device, and is able to provide larger amplitude currents to remove the DC offset more quickly.

20 Claims, 18 Drawing Sheets

(56) References Cited

U.S. PATENT DOCUMENTS

| | | | |
|---|---|---|---|
| 5,702,429 | A | 12/1997 | King |
| 5,902,236 | A | 5/1999 | Iversen |
| 5,902,249 | A | 5/1999 | Lyster |
| 5,913,882 | A | 6/1999 | King |
| 6,181,969 | B1 | 1/2001 | Gord |
| 6,516,227 | B1 | 2/2003 | Meadows et al. |
| 7,024,247 | B2 | 4/2006 | Gliner et al. |
| 7,424,322 | B2 | 9/2008 | Lombardi et al. |
| 7,450,992 | B1 | 11/2008 | Cameron |
| 8,255,057 | B2 | 8/2012 | Fang et al. |
| 8,335,664 | B2 | 12/2012 | Eberle |
| 8,352,030 | B2 | 1/2013 | Denison |
| 8,606,362 | B2 | 12/2013 | He et al. |
| 8,620,436 | B2 | 12/2013 | Parramon et al. |
| 9,044,155 | B2 | 6/2015 | Strahl |
| 9,155,892 | B2 | 10/2015 | Parker et al. |
| 9,248,274 | B2 | 2/2016 | Troosters et al. |
| 9,248,279 | B2 | 2/2016 | Chen et al. |
| 9,259,574 | B2 | 2/2016 | Aghassian et al. |
| 9,265,431 | B2 | 2/2016 | Hincapie Ordonez et al. |
| 9,302,112 | B2 | 4/2016 | Bornzin et al. |
| 9,381,356 | B2 | 7/2016 | Parker et al. |
| 9,386,934 | B2 | 7/2016 | Parker et al. |
| 9,403,013 | B2 | 8/2016 | Walker et al. |
| 9,409,020 | B2 | 8/2016 | Parker |
| 9,526,897 | B2 | 12/2016 | Chen et al. |
| 9,533,148 | B2 | 1/2017 | Carcieri |
| 9,731,116 | B2 | 8/2017 | Chen |
| 9,872,990 | B2 | 1/2018 | Parker et al. |
| 9,974,455 | B2 | 5/2018 | Parker et al. |
| 10,076,667 | B2 | 9/2018 | Kaula et al. |
| 10,716,937 | B2 | 7/2020 | Feldman et al. |
| 10,792,491 | B2 | 10/2020 | Feldman et al. |
| 10,881,859 | B2 | 1/2021 | Brill et al. |
| 10,926,097 | B2 | 2/2021 | Zhang et al. |
| 11,040,202 | B2 | 6/2021 | Marnfeldt |
| 2002/0156513 | A1 | 10/2002 | Borkan |
| 2005/0107674 | A1* | 5/2005 | Parthasarathy .......... A61B 5/30 600/301 |
| 2005/0246004 | A1 | 11/2005 | Cameron et al. |
| 2008/0146894 | A1 | 6/2008 | Bulkes et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0289665 | A1 | 10/2013 | Marnfeldt et al. |
| 2014/0194772 | A1 | 7/2014 | Single et al. |
| 2014/0236042 | A1 | 8/2014 | Parker et al. |
| 2014/0296737 | A1 | 10/2014 | Parker et al. |
| 2015/0080982 | A1 | 3/2015 | Funderburk |
| 2015/0157861 | A1 | 6/2015 | Aghassian |
| 2015/0223710 | A1 | 8/2015 | Cong et al. |
| 2015/0231402 | A1 | 8/2015 | Aghassian |
| 2015/0282725 | A1 | 10/2015 | Single |
| 2015/0313487 | A1 | 11/2015 | Single et al. |
| 2015/0360038 | A1 | 12/2015 | Zottola et al. |
| 2016/0166164 | A1 | 6/2016 | Obradovic et al. |
| 2016/0287126 | A1 | 10/2016 | Parker et al. |
| 2016/0287182 | A1 | 10/2016 | Single |
| 2017/0042482 | A1 | 2/2017 | Gunderson et al. |
| 2017/0049345 | A1 | 2/2017 | Single |
| 2017/0071490 | A1 | 3/2017 | Parker et al. |
| 2017/0135624 | A1 | 5/2017 | Parker |
| 2017/0216587 | A1 | 8/2017 | Parker |
| 2017/0274213 | A1 | 9/2017 | Ghosh et al. |
| 2017/0296823 | A1 | 10/2017 | Hershey et al. |
| 2017/0361101 | A1 | 12/2017 | Single |
| 2018/0071520 | A1 | 3/2018 | Weerakoon et al. |
| 2018/0071527 | A1 | 3/2018 | Feldman et al. |
| 2018/0110987 | A1 | 4/2018 | Parker |
| 2018/0117335 | A1 | 5/2018 | Parker et al. |
| 2018/0132747 | A1 | 5/2018 | Parker et al. |
| 2018/0132760 | A1 | 5/2018 | Parker |
| 2018/0133459 | A1 | 5/2018 | Parker et al. |
| 2018/0140831 | A1 | 5/2018 | Feldman et al. |
| 2018/0228391 | A1 | 8/2018 | Parker et al. |
| 2018/0228547 | A1 | 8/2018 | Parker et al. |
| 2018/0256052 | A1 | 9/2018 | Parker et al. |
| 2019/0076645 | A1 | 3/2019 | Bower et al. |
| 2019/0099602 | A1 | 4/2019 | Esteller et al. |
| 2019/0175915 | A1 | 6/2019 | Brill et al. |
| 2019/0209844 | A1 | 7/2019 | Esteller et al. |
| 2019/0275331 | A1 | 9/2019 | Zhu |
| 2019/0290900 | A1 | 9/2019 | Esteller et al. |
| 2019/0299006 | A1 | 10/2019 | Marnfeldt |
| 2019/0307341 | A1 | 10/2019 | Parker et al. |
| 2019/0366094 | A1 | 12/2019 | Esteller et al. |
| 2020/0155019 | A1 | 5/2020 | Esteller et al. |
| 2020/0305744 | A1 | 10/2020 | Weerakoon et al. |
| 2020/0305745 | A1 | 10/2020 | Wagenbach et al. |
| 2021/0236829 | A1 | 8/2021 | Zhang et al. |
| 2022/0040486 | A1 | 2/2022 | Moffitt |
| 2022/0266027 | A1* | 8/2022 | Zhang ................ A61N 1/36139 |
| 2023/0138443 | A1 | 5/2023 | Marnfeldt |
| 2023/0173273 | A1 | 6/2023 | Weerakoon et al. |

FOREIGN PATENT DOCUMENTS

| | | | |
|---|---|---|---|
| WO | WO-2016054274 A1 * | 4/2016 | ............... A61B 5/30 |
| WO | 2017/100866 | 6/2017 | |
| WO | 2017/173493 | 10/2017 | |
| WO | 2017/210352 | 12/2017 | |
| WO | 2017/219096 | 12/2017 | |
| WO | WO-2017214638 A1 * | 12/2017 | ......... A61N 1/36007 |
| WO | 2021/046120 | 3/2021 | |

* cited by examiner

USING STIMULATION CIRCUITRY TO PROVIDE DC OFFSET COMPENSATION AT INPUTS TO SENSE AMP CIRCUITRY IN A STIMULATOR DEVICE

CROSS REFERENCE TO RELATED APPLICATIONS

This is a non-provisional of U.S. Provisional Patent Application Ser. No. 63/371,705, filed Aug. 17, 2022, which is incorporated herein by reference, and to which priority is claimed.

FIELD OF THE INVENTION

This application relates to Implantable Medical Devices (IMDs), and more specifically to circuitry to assist with sensing neural responses to stimulation in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) or Deep Brain Stimulation (DBS) system. However, the present invention may find applicability with any stimulator device system.

A stimulator system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12, or some conductive portion of the case, can also comprise an electrode (Ec). In an SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In a DBS application, the electrode leads are implanted in the brain through holes in the skull, and lead extension are used to connect the leads to the IPG which is typically implanted under the clavicle (collarbone). In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. SCS therapy can relieve symptoms such as chronic back pain, while DBS therapy can alleviate Parkinsonian symptoms such as tremor and rigidity. IPGs as described should be understood as including External Trial Stimulators (ETSs), which mimic operation of the IPG during trials periods when leads have been implanted in the patient but the IPG has not. See, e.g., U.S. Pat. No. 9,259,574 (disclosing an ETS).

IPG 10 can include an antenna 27*a* allowing it to communicate bi-directionally with a number of external devices discussed subsequently. Antenna 27*a* as shown comprises a conductive coil within the case 12, although the coil antenna 27*a* can also appear in the header 23. When antenna 27*a* is configured as a coil, communication with external devices preferably occurs using near-field magnetic induction. IPG 10 may also include a Radio-Frequency (RF) antenna 27*b*. In FIG. 1, RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases (30*i*), as shown in the example of FIG. 2A. Stimulation parameters typically include amplitude (current I, although a voltage amplitude V can also be used); frequency (F); pulse width (PW); the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during its first phase 30*a*), and thus provides pulses which source a positive current of amplitude +I to the tissue. Electrode E2 has been selected as a cathode (again during first phase 30*a*), and thus provides pulses which sink a corresponding negative current of amplitude −I from the tissue. This is an example of bipolar stimulation, in which the lead includes one anode pole and one cathode pole. Note that more than one electrode on the lead may be selected to act as an anode electrode to form an anode pole at a given time, and more than one electrode may be selected to act as a cathode to form a cathode pole at a given time, as explained further in U.S. Pat. No. 10,881,859. Stimulation provided by the IPG 10 can also be monopolar. In monopolar stimulation, the lead is programmed with a single pole of a given polarity (e.g., a cathode pole), with the conductive case electrode Ec acting as a return (e.g., an anode pole). Again, more than one electrode on the lead may be active to form the pole during monopolar stimulation.

IPG 10 as mentioned includes stimulation circuitry 28 to form prescribed stimulation at a patient's tissue. FIG. 3 shows an example of stimulation circuitry 28, which includes one or more current source circuits and one or more current sink circuits. The sources and sinks can comprise Digital-to-Analog converters (DACs), and may be referred to as PDACs and NDACs in accordance with the Positive (sourced, anodic) and Negative (sunk, cathodic) currents they respectively issue. In the example shown, a NDACi/PDACi pair is dedicated (hardwired) to a particular electrode node ei 39. Each electrode node ei 39 is associated with an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation as explained above. PDACs and NDACs can also comprise voltage sources.

Proper control of the PDACs and NDACs allows any of the electrodes 16 to act as anodes or cathodes to create a current through a patient's tissue, R, hopefully with good therapeutic effect. Consistent with the example provided in FIG. 2A, FIG. 3 shows operation during the first phase 30*a* in which electrode E1 has been selected as an anode electrode to source current I to the tissue R and E2 has been selected as a cathode electrode to sink current from the tissue. Thus PDAC1 and NDAC2 are digitally programmed to produce the desired current, I, with the correct timing (e.g., in accordance with the prescribed frequency and pulse widths). As mentioned above, more than one anode electrode and more than one cathode electrode may be selected at one time, and thus current can flow through the tissue R between two or more of the electrodes 16. Other stimulation circuitries 28 can also be used in the IPG 10, including ones that includes switching matrices between the electrode nodes ei 39 and the N/PDACs. See, e.g., U.S. Pat. Nos. 6,181,969, 8,606,362, 8,620,436, 11,040,192, and 10,912,942. Much of the stimulation circuitry 28 of FIG. 3, including the PDACs and NDACs, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated herein by reference. As explained in these references, ASIC(s) may also contain other circuitry useful in the IPG 10, such as IPG master control circuitry 102 (see FIG. 5), telemetry circuitry (for interfacing off chip with telemetry antennas 27*a* and/or 27*b*), circuitry for generating the compliance voltage VH (as explained next), various measurement circuits, etc.

Power for the stimulation circuitry 28 is provided by a compliance voltage VH, as described in further detail in U.S. Patent Application Publications 2013/0289665 and 2018/0071520. The compliance voltage VH may be coupled to the source circuitry (e.g., the PDAC(s)), while ground may be coupled to the sink circuitry (e.g., the NDAC(s)), such that the stimulation circuitry 28 is powered by VH and ground. Other power supply voltages may be used with the PDACs and NDACs, and explained in U.S. Patent Application Publication 2018/0071520, but these aren't shown in FIG. 3 for simplicity.

Preferably, and as described in U.S. Pat. No. 11,040,202, the compliance voltage VH can be produced by a VH regulator 49. VH regulator 49 receives the voltage of the battery 14 (Vbat) and boost this voltage to a higher value required for the compliance voltage VH. VH regulator 49 can comprise an inductor-based boost converter or a capacitor-based charge pump for example. The regulator 49 can vary the value of VH based on measurements taken from the stimulation circuitry 28 as explained in detail in the '202 patent. Using such measurements allows VH to be established at an energy-efficient level: high enough to form the prescribed current without loading (i.e., without producing less current that prescribed), yet low enough to not needlessly waste power in the stimulation circuitry 28 when forming the prescribed current. In this respect, VH can be variable, and typically ranges from about 5 to 15 Volts.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861. While useful, DC-blocking capacitors 38 are not strictly required in all IPG designs and applications.

Referring again to FIG. 2A, the stimulation pulses as shown are biphasic, with each pulse comprising a first phase 30*a* followed thereafter by a second phase 30*b* of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30*a*, charge will (primarily) build up across the DC-blockings capacitors C1 and C2 associated with the electrodes E1 and E2 used to produce the current, giving rise to voltages Vc1 and Vc2 (I=C*dV/dt). During the second pulse phase 30*b*, when the polarity of the current I is reversed at the selected electrodes E1 and E2, the stored charge on capacitors C1 and C2 is recovered, and thus voltages Vc1 and Vc2 are intended to return to 0V at the end the second pulse phase 30*b*. Typically, the biphasic pulses used are programmed as charge balanced because charge of each of the pulses phases (+Q and −Q) are equal, and thus cancel to zero.

Charge recovery using phases 30*a* and 30*b* is said to be "active" because the P/NDACs in stimulation circuitry 28 actively drive a current, in particular during the last phase 30*b* to recover charge stored after the first phase 30*a*. However, because the current sources may not be perfectly balanced or other factors, such active charge recovery may not be perfect, and some residual charge may be present in capacitive structures even after phase 30*b* is completed. Accordingly, the stimulation circuitry 28 can also provide for passive charge recovery. Passive charge recovery is implemented using passive charge recovery switches PRi 41 as shown in FIG. 3. These switches 41 when selected via assertion of control signals <Xi> couple each desired electrode node ei to a passive recovery voltage Vpr established on bus 43. As explained in U.S. Pat. No. 10,716,937 and 10,792,491, this allows any stored charge to be recovered through the patient's tissue, R, passive and without the P/NDACs in stimulation circuitry 28 actively driving a current. Control signals <Xi> are usually asserted to cause passive charge recovery after each pulse (e.g., after each last phase 30*b*) during periods 30*c* shown in FIG. 2A. Because passive charge recovery involves capacitive discharge through the resistance R of the patient's tissue, such discharge manifests as an exponential decay in current, as shown in FIG. 2A. As also discussed in the '937 patent, each of the passive charge recovery switches 41 can be associated with a variable resistance, and as such each switch 41 can be controlled by a bus of signals <Xi> to control the resistance at which passive charge recovery occurs—i.e., the on resistance of the switches 41 when they are closed.

Passive charge recovery during period 30*c* may be followed by a quiet period 30*d* during which no active current is driven by the DAC circuitry, and none of the passive recovery switches 41 are closed. This quiet period 30*d* may last until the next pulse is actively produced (e.g., phase 30*a*). Like the particulars of pulse phases 30*a* and 30*b*, the occurrence of passive charge recovery (30*c*) and any quiet periods (30*d*) can be prescribed as part of the stimulation program.

FIG. 4 shows various external systems 60, 70, and 80 that can wirelessly communicate data with the IPG 10. Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information, etc.

External controller 60 can be as described in U.S. Patent Application Publication 2015/0080982 for example, and may comprise a portable, hand-held controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a display 61 and a means for entering commands, such as buttons 62 or selectable graphical icons provided on the display 61. The external controller 60's user interface enables a patient to adjust stimulation parameters, although it may have limited functionality when compared to systems 70 and 80, described shortly. The external controller 60 can have one or more antennas capable of communicating with the IPG 10. For example, the external controller 60 can have a near-field magnetic-induction coil antenna 64*a* capable of wirelessly communicating with the coil antenna 27*a* in the IPG 10. The external controller 60 can also have a far-field RF antenna 64*b* capable of wirelessly communicating with the RF antenna 27*b* in the IPG 10.

Clinician programmer 70 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 71, buttons 72, as well as other user-interface devices such as a mouse, a keyboard, speakers, a stylus, a printer, etc., not all of which are shown for convenience. Also shown in FIG. 4 are accessory devices for the clinician programmer 70 that are usually specific to its operation as a stimulation controller, such as a communication "wand" 76 coupleable to suitable ports on the computing device. The antenna used in the clinician programmer 70 to communicate with the IPG 10 can depend on the type of antennas included in the IPG 10. If the patient's IPG 10 includes a coil antenna 27*a*, wand 76 can likewise include a coil antenna 74*a* to establish near-field magnetic-induction communications at small distances. In this instance, the wand 76 may be affixed in close proximity to the patient, such as by placing the wand 76 in a belt or holster wearable by the patient and proximate to the patient's IPG 10. If the IPG 10 includes an RF antenna 27*b*, the wand 76, the computing device, or both, can likewise include an RF antenna 74*b* to establish communication with the IPG 10 at larger distances. The clinician programmer 70 can also communicate with other devices and networks, such as the Internet, either wirelessly or via a wired link provided at an Ethernet or network port.

External system 80 comprises another means of communicating with and controlling the IPG 10 via a network 85 which can include the Internet. The network 85 can include a server 86 programmed with communication and control functionality, and may include other communication networks or links such as WiFi, cellular or land-line phone links, etc. The network 85 ultimately connects to an intermediary device 82 having antennas suitable for communication with the IPG's antenna, such as a near-field magnetic-induction coil antenna 84*a* and/or a far-field RF antenna 84*b*. Intermediary device 82 may be located generally proximate to the IPG 10. Network 85 can be accessed by any user terminal 87, which typically comprises a computer device associated with a display 88. External system 80 allows a remote user at terminal 87 to communicate with and control the IPG 10 via the intermediary device 82.

FIG. 4 also shows circuitry 90 involved in any of external systems 60, 70, or 80. Such circuitry can include control circuitry 92, which can comprise any number of devices such as one or more microprocessors, microcomputers, FPGAs, DSPs, other digital logic structures, etc., which are capable of executing programs in a computing device. Such control circuitry 92 may contain or coupled with memory 94 which can store external system software 96 for controlling and communicating with the IPG 10, and for rendering a Graphical User Interface (GUI) 99 on a display (61, 71, 88) associated with the external system. In external system 80, the external system software 96 would likely reside in the server 86, while the control circuitry 92 could be present in either or both of the server 86 or the terminal 87.

SUMMARY

A stimulator device is disclosed, which may comprise: a plurality of electrode nodes, wherein each of the electrode nodes is associated with a different electrode configured to contact a patient's tissue; stimulation circuitry configurable to provide stimulation to one or more of the plurality of electrode nodes to provide stimulation to the patient's tissue; sense amplifier circuitry comprising a first input and a second input, wherein the sense amplifier circuitry is configurable to receive one of the plurality of electrode nodes at the first input, wherein the sense amplifier circuitry is configured to sense a tissue signal; a detector configured to produce data indicative of the DC offset voltage between the first input and the second input; and control circuitry configured to use the data to control the stimulation circuitry to issue a compensating current at the first input, the second input, or both of the first and second inputs, to reduce or eliminate the DC offset voltage.

In one example, the stimulator device may further comprise a DC-blocking capacitor between each of the electrode nodes and its associated electrode. In one example, the compensating current reduces or eliminates the DC offset voltage by charging or discharging the DC-blocking capacitor associated with the first input. In one example, the one electrode node received at the first input is different from the one or more electrode nodes that provide the stimulation to the patient's tissue. In one example, the one electrode node received at the first input comprises one of the one or more electrode nodes that provide the stimulation to the patient's tissue. In one example, the sense amplifier circuitry is configured to sense a neural response to the stimulation as the tissue signal. In one example, the sense amplifier circuitry is configurable to receive another one of the plurality of electrode nodes at the second input. In one example, the control circuitry is configured to issue the compensating current at the first and second inputs to reduce or eliminate the DC offset voltage. In one example, the compensating currents at the first and second inputs are of opposite polarities. In one example, the electrode nodes received at the first and second inputs are different from the one or more electrode nodes that provide the stimulation to the patient's tissue. In one example, the electrode nodes received at the first and second inputs comprise the one or more electrode nodes that provide the stimulation to the patient's tissue. In one example, the compensating current comprises one or more charge imbalanced pulses. In one example, the control circuitry comprises an algorithm to control the stimulation circuitry to issue the compensating current. In one example, the algorithm is configured to iterate by periodically producing the data indicative of the DC offset voltage, and periodically using the data to control the stimulation circuitry to issue the compensating current. In one example, a charge of the compensating current is adjusted as the algorithm iterates. In one example, the charge of the compensating current is reduced as the algorithm iterates. In one example, at least one initial iteration provides a coarse adjustment to the DC offset voltage, and wherein at least one later iteration provides a fine adjustment to the DC offset voltage. In one example, the algorithm is configured to calculate a charge using the data that eliminates the DC offset voltage, and to control the stimulation circuitry to issue the compensating current with the calculated charge. In one example, the stimulator device further comprises DC offset compensating circuitry configured to issue a DC current. In one example, the algorithm is further configured to enable the DC offset compensation circuitry to issue the DC current at the first input or the second input to reduce or eliminate the DC offset voltage. In one example, the stimulation circuitry is configurable to provide the stimulation to the one or more of the electrode nodes in accordance with a stimulation program. In one example, the detector comprises an Analog-to-Digital Converter (ADC). In one example, the ADC provides a digitized value indicative of the DC offset voltage as the data. In one example, the stimulator device further comprises an ADC configured to produce a digitized waveform of the sensed tissue signal, wherein the digitized waveform comprises a plurality of samples. In one example, the detector is configured to determine whether the digitized waveform is saturated. In one example, the data indicative of the DC offset voltage comprises an indication of high saturation or low saturation. In one example, the indication of high saturation comprises a determination that one or more samples in the digitized waveform are pinned to a maximum of an operating range of the ADC, and wherein the indication of low saturation comprises a determination that one or more samples in the digitized waveform are pinned to a minimum of the operating range of the ADC. In one example, the data comprises one or more digital signals indicative of saturation. In one example, the data comprises a first digital signal indicative of high saturation, and a second digital signal indicative of low saturation. In one example, the detector comprises a window comparator to produce the first and second digital signals.

A method is disclosed for operating a stimulator device comprising a plurality of electrode nodes, wherein each of the electrode nodes is associated with a different electrode configured to contact a patient's tissue. The method may comprise: providing stimulation in accordance with a stimulation program from stimulation circuitry to one or more of the plurality of electrode nodes to provide stimulation to the patient's tissue; using sense amplifier circuitry to sense a tissue signal, the sense amplifier circuitry comprising a first input and a second input, wherein the sense amplifier circuitry receives one of the plurality of electrode nodes at the first input; and controlling the stimulation circuitry to issue a compensating current at the first input, the second input, or both of the first and second inputs, to reduce or eliminate a DC offset voltage between the first input and the second input.

In one example, the stimulator device further comprises a DC-blocking capacitor between each of the electrode nodes and its associated electrode. In one example, the compensating current reduces or eliminates the DC offset voltage by charging or discharging the DC-blocking capacitor associated with the first input. In one example, the one electrode node received at the first input is different from the one or more electrode nodes that provide the stimulation to the patient's tissue. In one example, the one electrode node received at the first input comprises one of the one or more electrode nodes that provide the stimulation to the patient's tissue. In one example, the sense amplifier circuitry is configured to sense a neural response to the stimulation as the tissue signal. In one example, the sense amplifier circuitry receives another one of the plurality of electrode nodes at the second input. In one example, the compensating current is issued at the first and second inputs to reduce or eliminate the DC offset voltage. In one example, the compensating currents at the first and second inputs are of opposite polarities. In one example, the electrode nodes received at the first and second inputs are different from the one or more electrode nodes that provide the stimulation to the patient's tissue. In one example, the electrode nodes received at the first and second inputs comprise the one or more electrode nodes that provide the stimulation to the patient's tissue. In one example, the compensating currents at the first and second inputs are of opposite polarities but have the same amplitude. In one example, the compensating current comprises one or more charge imbalanced pulses. In one example, an algorithm operable in the stimulation device controls the stimulation circuitry to issue the compensating current. In one example, the algorithm controls the stimulation circuitry iteratively to issue the compensating current. In one example, a charge of the compensating current is adjusted as the algorithm iterates. In one example, the charge of the compensating current is reduced as the algorithm iterates. In one example, at least one initial iteration provides a coarse adjustment to the DC offset voltage, and wherein at least one later iteration provides a fine adjustment to the DC offset voltage. In one example, the algorithm calculates a charge using the data that eliminates the DC offset voltage, and controls the stimulation circuitry to issue the compensating current with the calculated charge. In one example, the stimulator device further comprises DC offset compensating circuitry for issuing a DC current. In one example, the algorithm operable in the stimulation device further controls the DC offset compensation circuitry to issue the DC current at the first input or the second input to reduce or eliminate the DC offset voltage. In one example, the stimulator device further comprises an Analog-to-Digital Converter (ADC) to produce a digitized value indicative of the DC offset voltage between the first input and the second input. In one example, the stimulation circuitry is controlled to issue the compensating current in accordance with the digitized value. In one example, the stimulator device further comprises an Analog-to-Digital Converter (ADC) to produce a digitized waveform of the sensed tissue signal, wherein the digitized waveform comprises a plurality of samples. In one example, the method further comprises determining whether the digitized waveform is saturated. In one example, the stimulation circuitry is controlled to issue the compensating current in accordance with the determination whether the digitized waveform is saturated. In one example, the method further comprises determining a first digital signal indicative of high saturation of the DC offset voltage, and a second digital signal indicative of low saturation of the DC offset voltage. In one example, the stimulation circuitry is controlled to issue the compensating current in accordance with the first and second digital signals.

BRIEF DESCRIPTION OF THE DRAWINGS

FIG. 10A shows a first example of a DC offset compensation algorithm, while

DETAILED DESCRIPTION

An increasingly interesting development in pulse generator systems is the addition of sensing capability to complement the stimulation that such systems provide. For example, and as explained in U.S. Patent Application Publication 2021/0236829, it can be beneficial to sense a neural response produced by neural tissue that has received stimulation from an IPG. The '829 Publication shows an example where sensing of neural responses is useful in an SCS context, and in particular discusses the sensing of Evoked Compound Action Potentials, or "ECAPs," in a patient's spinal cord. U.S. Patent Application Publication 2022/0040486 shows an example where sensing of neural responses is useful in a DBS context, and in particular discusses the sensing of Evoked Resonant Neural Activity, or "ERNA," in a patient's brain. The '829 Publication further discusses the sensing of stimulation artifacts caused by stimulation, as discussed further below. Still further, pulse generator systems may sense other biometric signals from a patient's tissue. Collectively, any of these sensed signals from the tissue comprise a tissue signal in a stimulator system. Discussion below largely focuses on the sensing of an ECAP neural response as a tissue signal of interest as a convenient example.

Figure 5:
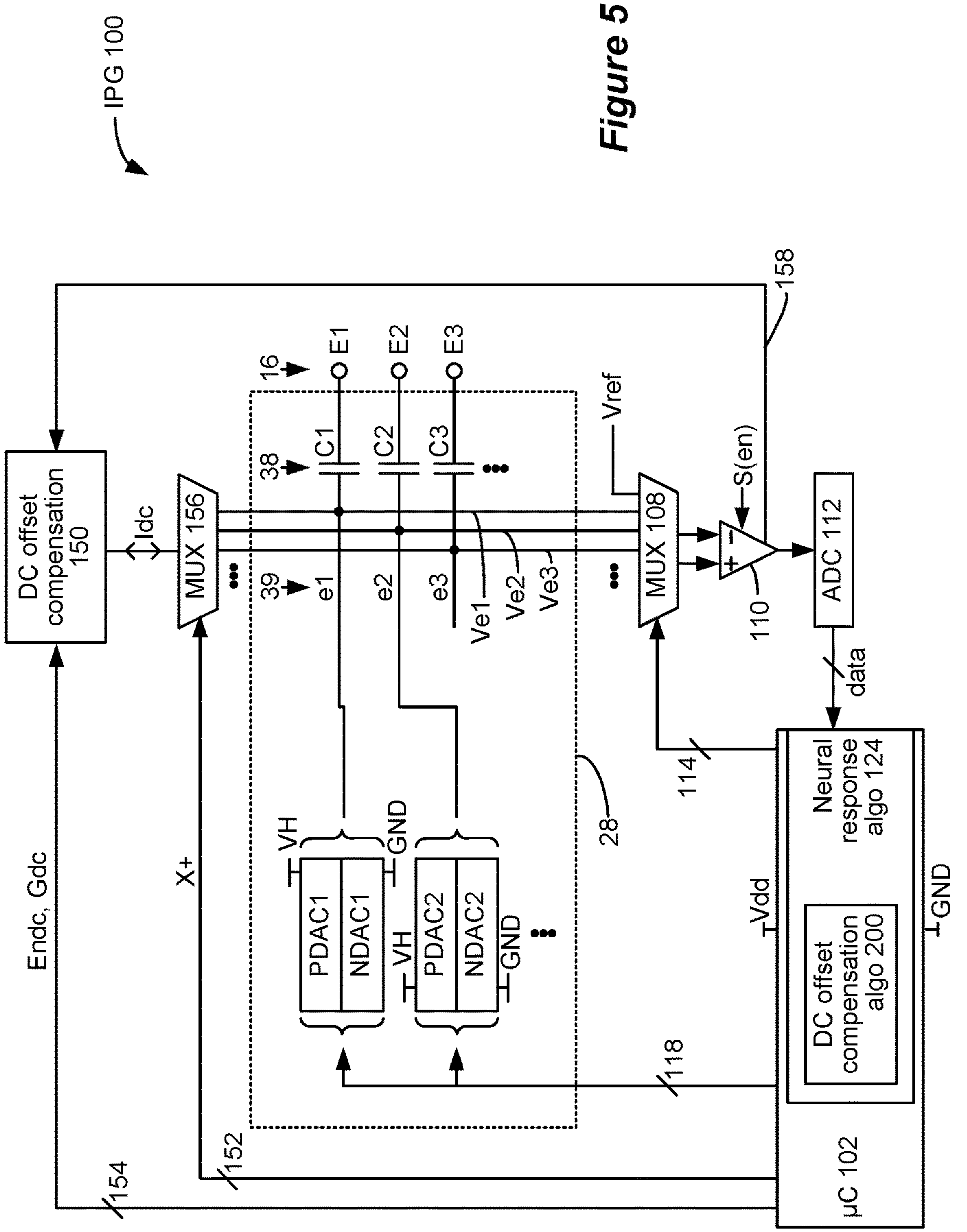
FIG. 5 shows an IPG having neural response sensing capability.

FIG. 5 shows basic circuitry for sensing tissue signals such as neural responses in an IPG 100. The IPG 100 includes control circuitry 102, which may comprise a microcontroller for example, such as Part Number MSP430, manufactured by Texas Instruments, which is described in data sheets accessible on the Internet. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs) in the IPG 10 as described earlier, which ASIC(s) may additionally include the other circuitry shown in FIG. 5.

Figure 3:
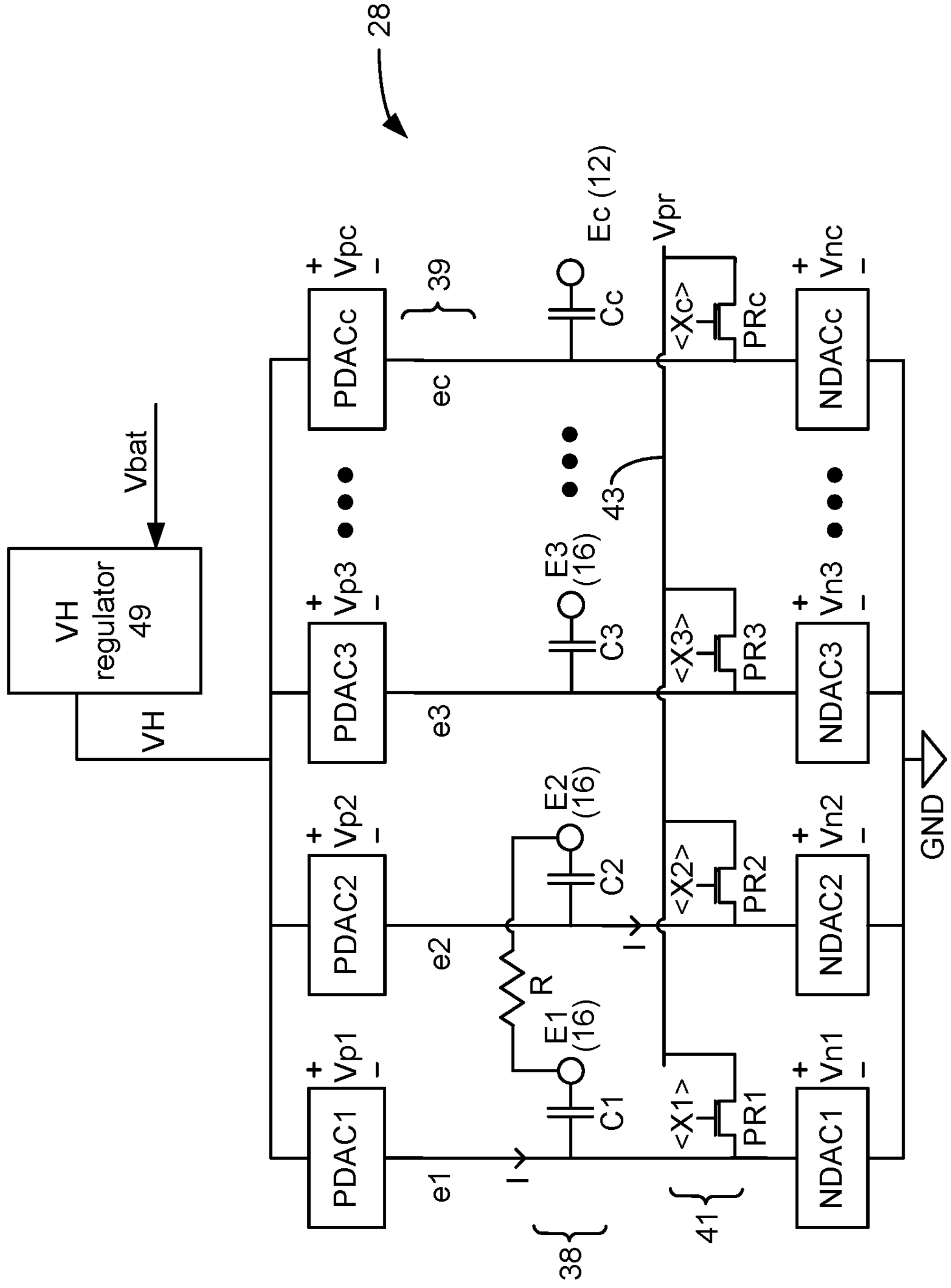
Figure 3 (prior art)
FIG. 3 shows stimulation circuitry useable in the IPG, in accordance with the prior art.

FIG. 5 includes the stimulation circuitry 28 described earlier (FIG. 3), including one or more DACs (PDACs and NDACs). A bus 118 provides digital control signals to the DACs to produce currents or voltages of prescribed amplitudes and with the correct timing at the electrodes selected for stimulation. The electrode current paths to the electrodes 16 include the DC-blocking capacitors 38 described earlier.

Figure 4:
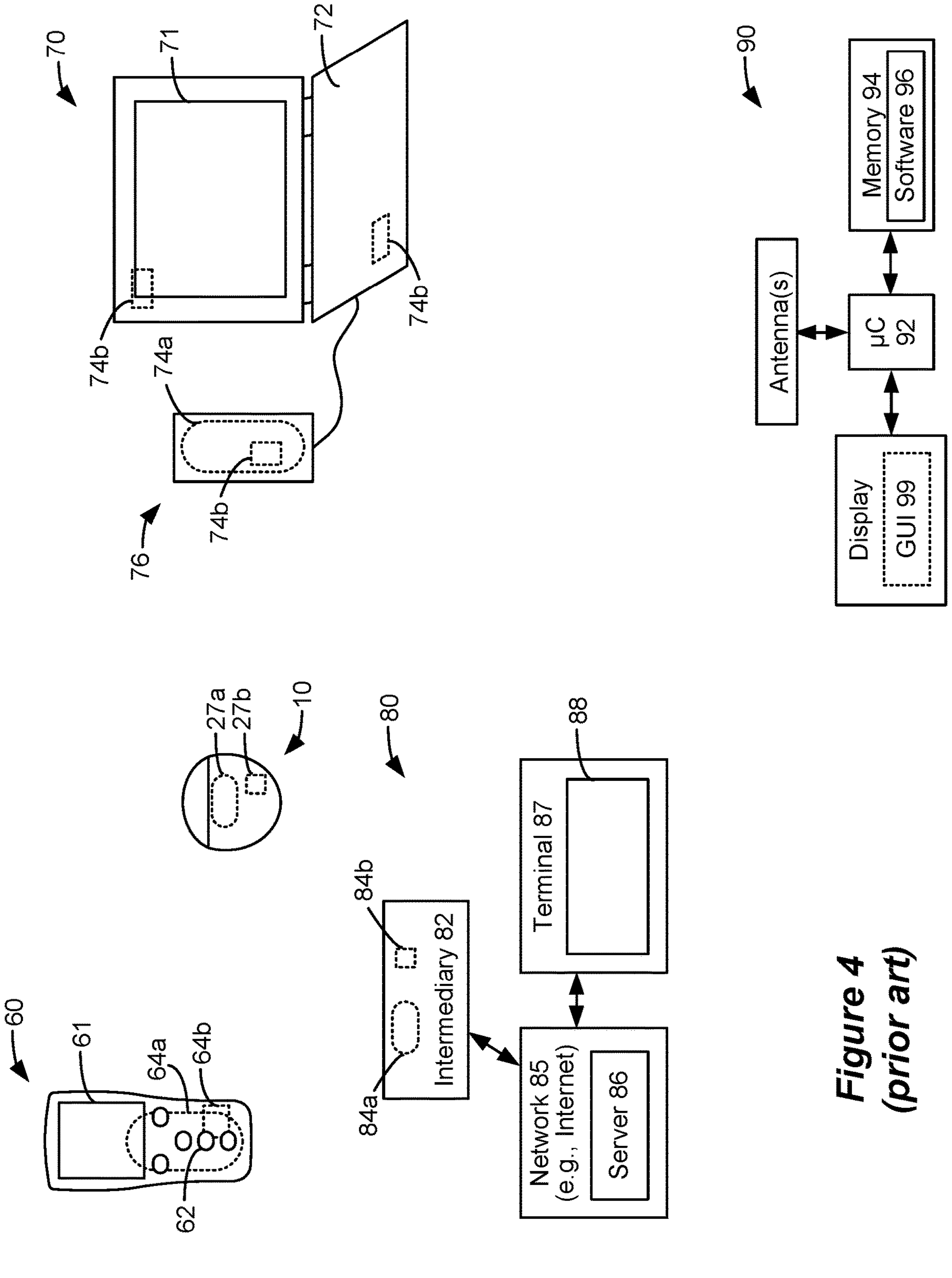
Figure 4 (prior art)
FIG. 4 shows various external devices capable of communicating with and programming stimulation in an IPG, in accordance with the prior art.

FIG. 5 also shows circuitry used to sense tissue signals such as neural responses. As shown, the electrode nodes 39 are input to a multiplexer (MUX) 108. The MUX 108 is controlled by a bus 114, which operates to select one or more electrode nodes, and hence to designate corresponding electrodes 16 as sensing electrodes. The sensing electrode(s) selected via bus 114 can be determined automatically by control circuitry 102 and/or a neural response algorithm 124, as described further below. However, the sensing electrode(s) may also be selected by the user (e.g., a clinician) via an external system 60, 70 or 80 (FIG. 4).

Figure 6:
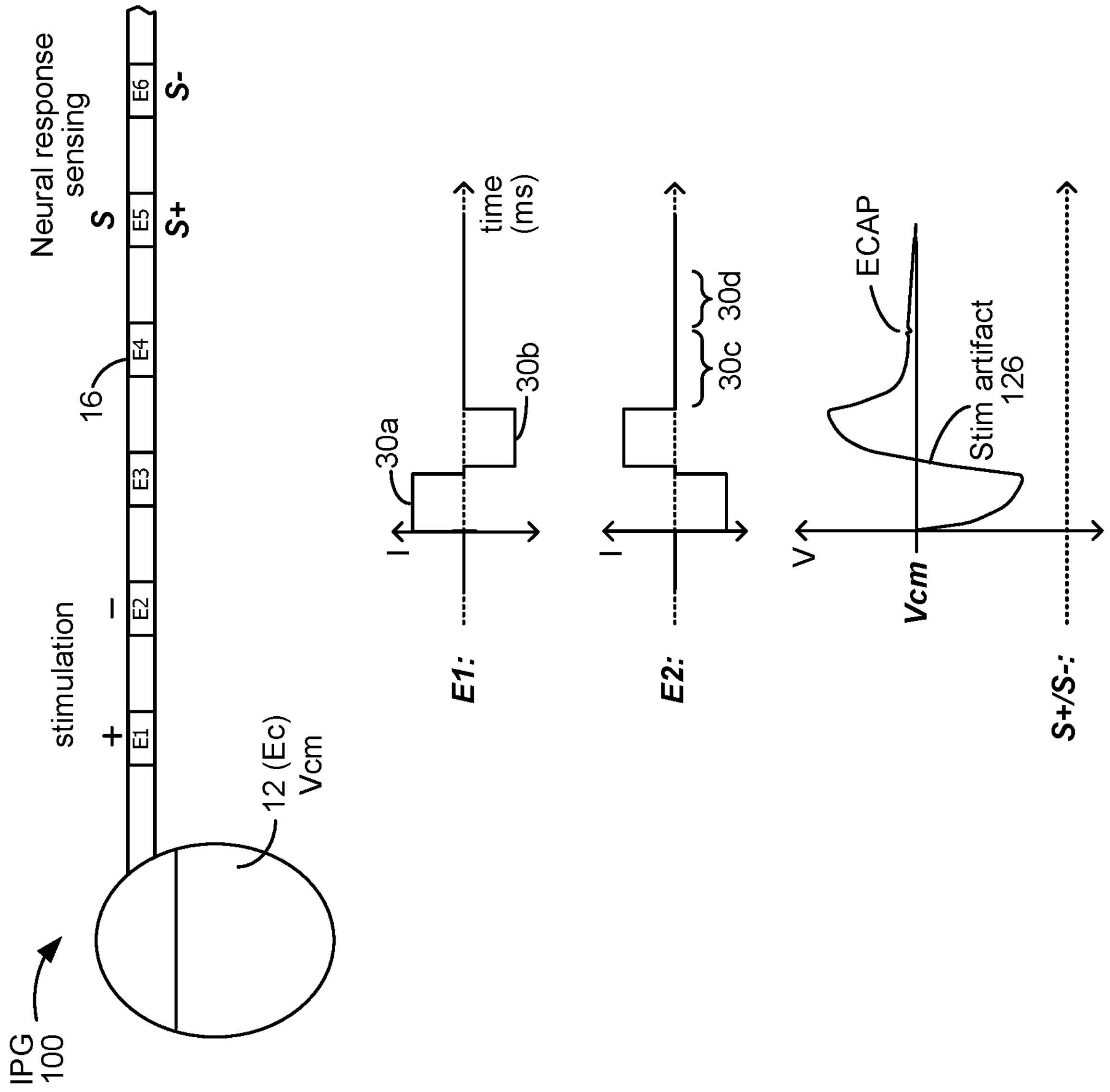
FIG. 6 shows stimulation producing a neural response, and the sensing of that neural response at at least one electrode of the IPG.

Electrodes selected as sensing electrodes are provided by the MUX 108 to a sense amplifier (amp) circuitry 110, and sensing can occur differentially using two sensing electrodes, or using a single sensing electrode. These examples are shown in FIG. 6. If single-ended sensing is used, a single electrode (e.g., E5) is selected as a single sensing electrode (S) and is provided to the positive input of the sense amp circuitry 110, where it is compared to a reference voltage Vref provided to the negative input. The reference voltage Vref can comprise any DC voltage produced within the IPG, such as ground, the voltage of the battery (Vbat), or some fraction of the compliance voltage VH (such as VH/2). If differential sensing is used, two electrodes (e.g., E5 and E6) are selected as sensing electrodes (S+ and S−) by the MUX 108, with one electrode (e.g., E5) provided to the positive input of the sense amp circuitry 110, and the other (e.g., E6) provided to the negative input. As explained in the '829 Publication, differential sensing can be useful to cancel any common mode DC voltages present in the tissue and reflected at the electrodes, such as voltages created by the stimulation itself—i.e., stimulation artifacts as explained further below.

Although only one sense amp circuit 110 is shown in FIG. 5 for simplicity, there could be more than one, such as a sense amp dedicated to each electrode node. In this case, MUX 108 would not be necessary, and each sense amp could be activated as needed depending on which electrodes are selected as sensing electrodes. In another example most useful for differential sensing, some number of sense amp circuitries 110 (e.g., four) can be provided, thus allowing any eight of the electrodes to be selected to act as sensing electrodes at a given time (e.g., by one or more MUXes 108). The timing at which sensing occurs can be affected by a sensing enable signal S(en). Further details of sense amp circuitry 110 are discussed later with reference to FIG. 7.

The analog waveform comprising the amplified tissue signal is preferably converted to digital signals by an Analog-to-Digital converter (ADC) 112, and input to the IPG's control circuitry 102. The ADC 112 can be included within the control circuitry 102's input stage as well. The control circuitry 102 can be programmed with a neural response algorithm 124 (or a tissue signal analyzer more generally) to evaluate the neural responses, and to take appropriate actions as a result. For example, the neural response algorithm 124 may change the stimulation in accordance with the sensed neural response, and can issue new control signals via bus 118 to change operation of the stimulation circuitry 28 to affect better treatment for the patient. As explained in the above referenced '829 Publication, the neural response algorithm 124 can extract features of the sensed neural response, such as various peak heights, line widths, areas, durations, etc., which may be used to control the stimulation as just described, to determine the effectiveness of stimulation treatment, or for other reasons.

The neural response algorithm 124 may also cause the selection of new sensing electrode(s), which can be affected by issuing new control signals on bus 114. Selecting optimal sensing electrode(s) can be important, and may be determined in light of stimulation that is being provided. In this regard, sensing electrodes may be selected near enough to the electrodes providing stimulation (e.g., E1 and E2) to allow for proper neural response sensing, but far enough from the stimulation (e.g., E5 and E6) that the stimulation doesn't substantially interfere with neural response sensing. See, e.g., U.S. Patent Application Publication 2020/0155019. This is particularly true when sensing ECAP neural responses during Spinal Cord Stimulation (SCS). However, this is not strictly required, and in some instances it can be beneficial to use at least one sensing electrode that is also used to provide stimulation, as discussed further below with reference to FIGS. 15A-15C.

Tissue signals such as neural responses to stimulation are typically small-amplitude AC signals on the order of microVolts or milliVolts, which can make sensing difficult. The sense amp circuitry 110 needs to be capable of resolving this small signal, and this is particularly difficult when one realizes that this small signal typically rides on a background voltage otherwise present in the tissue. As explained in U.S. Patent Application Publication 2020/0305744, which is incorporated by reference in its entirety, this background voltage can be caused by the stimulation itself. This is shown in the waveforms at the bottom of FIG. 6, which show the current stimulation pulses, and the signals received at selected sensing electrodes S+ or S−. The sensed signal from the tissue at the sensing electrode(s) includes a neural response—in this case an ECAP—and may also include a stimulation artifact 126 which results from the electromagnetic field that forms in the tissue as a result of the stimulation. The neural response (e.g., ECAP) may be present during active stimulation (e.g., during phases 30*a* or 30*b*) when the stimulation artifact is higher and perhaps varying more significantly, or after active stimulation (as shown in FIG. 6) when the stimulation artifact is lower or non-existent (e.g., during passive charge recovery 30*c* or quiet periods 30*d*). Because the stimulation circuitry 28 is powered by the compliance voltage VH and ground (see FIG. 3), the stimulation artifact 126 will vary between these voltages, and can comprise several Volts.

As noted above, differential sensing is useful because it allows the sense amp circuitry 110 to subtract any common mode voltages like the stimulation artifact 126 present in the tissue, hence making neural responses easier to resolve. However, this will not remove the stimulation artifact 126 completely, because the stimulation artifact 126 will not be exactly the same at each sensing electrode. Therefore, even when using differential sensing, it may be difficult to resolve the small tissue signals such as neural responses which may still ride on a significant background voltage.

U.S. Pat. No. 11,040,202, which is incorporated herein by reference in its entirety, describes tissue biasing circuitry that assists in tissue signal sensing by holding the tissue via a capacitor (such as one of the DC-blocking caps 38) to a common mode voltage, Vcm. This common mode voltage Vcm is preferably established at the conductive case electrode Ec as shown in FIG. 6, although another lead-based electrode could also be used to provide Vcm. See, e.g., U.S. Patent Application Publication 2023/0138443. As these references disclose, it is beneficial to establish Vcm with reference to the power supply voltage of the DAC circuitry—i.e., the compliance voltage VH explained earlier-because the voltages in the tissue will be between this voltage and ground. Preferably, Vcm can equal approximately VH/2. When a common mode voltage Vcm is provided to the tissue, AC tissue signals will also be referenced to this voltage. This is a helpful improvement, because it tends to stabilize the DC level of the signals being input to the sense amp circuitry 110 by the sensing electrodes.

Figure 7:
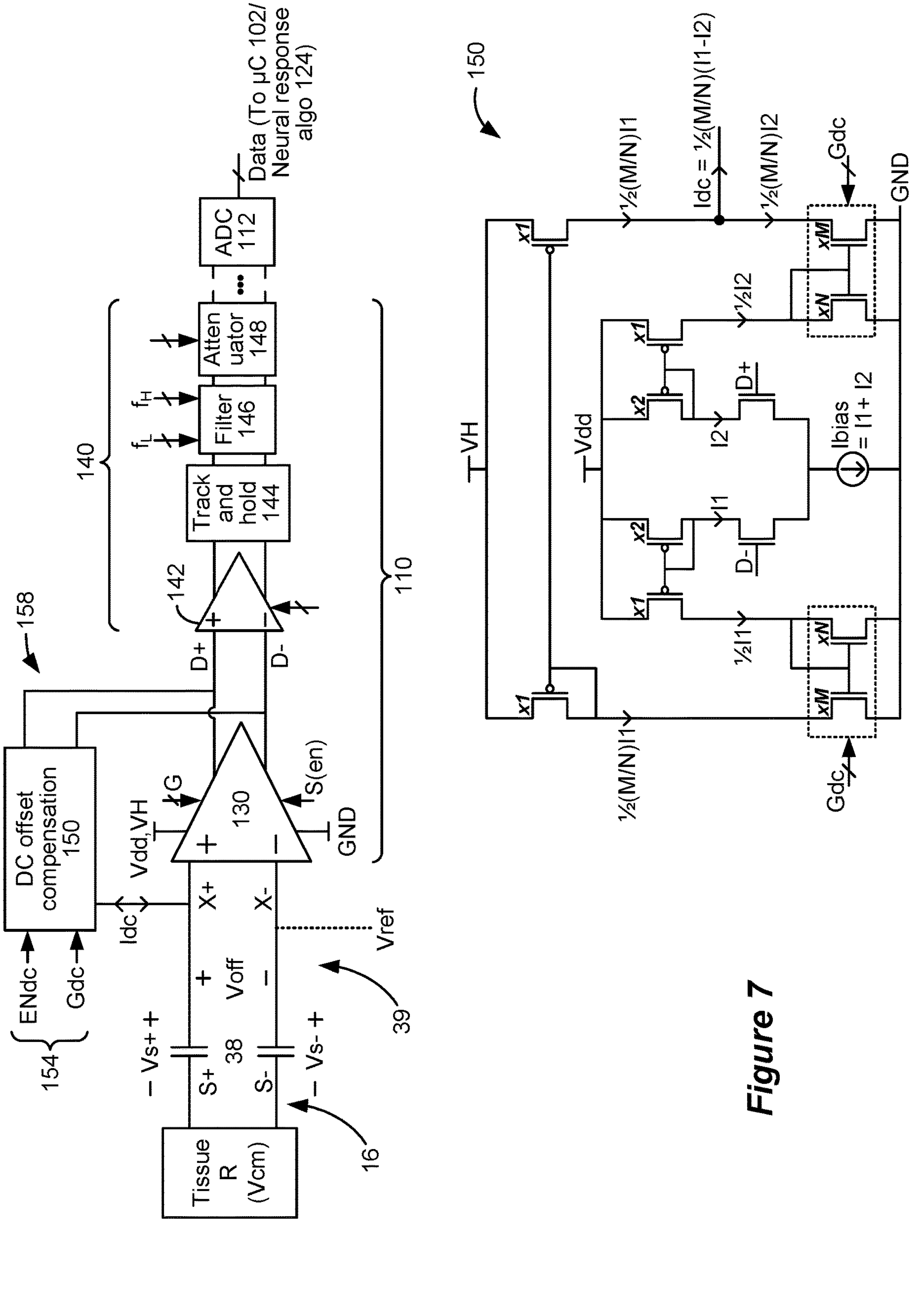
FIG. 7 shows sense amp circuitry useable in an IPG having sensing capability, and further shows DC offset compensation circuitry useable to remove any DC offset between the input signals.

FIG. 7 shows sense amp circuitry 110 in further detail, which includes a differential amplifier (diff amp) 130. The diff amp receives the electrodes nodes 39 (X+, X−) of the selected sensing electrodes (S+, S−, assuming differential sensing is used), with the DC-blocking capacitors 38 intervening between these nodes. (Vref would be used for single-ended sensing). The diff amp 130 may be powered by the compliance voltage VH, or a lower constant power supply otherwise operable in the IPG 100, such as Vdd (e.g., 3.3 V). The gain G of the diff amp 130—i.e., amplification imparted to a difference in the input voltages X+ and X− is programmable using control signals, and in one example the gain of the diff amp 130 can be adjusted from 1 to 200. Gain control signals (like other gains in the sense amp circuitry 110, discussed below) can either be set in firmware, by the control circuitry 102 (e.g., algorithm 124), or using an external system (FIG. 4) in communication with the IPG 100.

Although not shown, there may be more than one diff amp 130 that can be used for neural sensing. For example, as disclosed in U.S. Patent Application Publication 2023/0173273, which is incorporated by reference in its entirety, diff amp 130 can comprise both a low-voltage diff amp (powered by Vdd) and a high-voltage diff amp (powered by VH). Either of these diff amps can be selected to sense a neural response at different times and depending on the circumstances, which each having advantages and disadvantages. For example, if the DC level of the inputs X+ or X− is relatively high, the high-voltage diff amp can be selected; otherwise the low voltage diff amp can be used, which has lower noise performance. The '273 Publication discloses monitoring circuitry to sense the DC levels of the inputs and to select either the low- or high-voltage diff amp in this type of design. The single diff amp 130 shown in FIG. 7 can comprise either a low- or high-voltage diff amp.

The diff amp 130 outputs a differential analog output at outputs D− and D+ with the appropriate gain: V(D+)−V(D−)=G*(V(X+)−V(X−)). This differential output may be processed further by analog processing circuitry 140 before being digitized at the ADC 112. Processing circuitry 140 can include one or more additional diff amp(s) 142 connected in series to add additional gain to the sensed tissue signal. Track and hold circuitry 144 may also be included to hold the value of the analog outputs (e.g., during the stimulation artifact 126 if that signal is not of interest), which can be useful to prevent adverse operation of the filter circuitry 146 that follows. Filter circuitry 146 can remove frequencies from the sensed signal that are not of interest. Such excludable frequencies from the sensed tissue signals may be low (such as those resulting from other biological processes such as respiration or heart rhythms) and/or high (such as noise), and in this regard, filter 146 can comprise a band pass filter whose lower and upper frequencies ($f_L$, $f_H$) are programmable. Attenuator 148 can be used to reduce the gain of the sensed signal if necessary. This may be particularly useful if it is desired to sense the larger signals, such as the stimulation artifact 126, and as such the attenuator's 148 gain can be programmable to a value less than 1.

Analog processing circuitry 140 is not strictly necessary, and any or all of stages 142-148 could be excluded. Analog processing circuitry 140 could also include additional stages not shown in FIG. 7. Functions performed by the analog processing circuitry 140 may also be accomplished digitally (i.e., after digitization by the ADC 112), for example, within the control circuitry 102 and/or the neural response algorithm 124 (FIG. 5).

Sense amp circuitry 110 can include other improvements not shown in FIG. 7, but which are disclosed in the above-incorporated '273 Publication and '744 Publication. For example, the diff amp 130 be used in a well-known chopper amplifier configuration to reduce noise, and in particular 1/f noise, which is helpful in resolving small-signal neural responses. Further, to prevent damage to or improper operation of the diff amp 130, inputs X+ and X− can be provided with clamping circuits to keep the DC voltage on these inputs from exceeding a maximum voltage or falling below a minimum voltage. DC-level shifting circuits can also be used to reference signals X+ and X− to a DC voltage reference consistent with the input requirements of the diff amp 130.

As also shown in FIGS. 5 and 7, and as described in detail in the above-incorporated '273 Publication, the sense amp circuitry 110 can include or be coupled with DC offset compensation circuitry 150. The goal of this circuitry is to equate the DC voltages at the inputs X+ and X− of the sense amp circuitry. The difference in DC voltages at the inputs is generally not useful to sense (or amplify), because the sense amp circuitry 110 is generally concerned with sensing AC tissue signals such as neural responses. Use of DC offset compensation circuitry 150 may not always be required, and thus control signal ENdc may be received at the DC offset compensation circuitry 150 to selectively enable its use.

Figure 1:
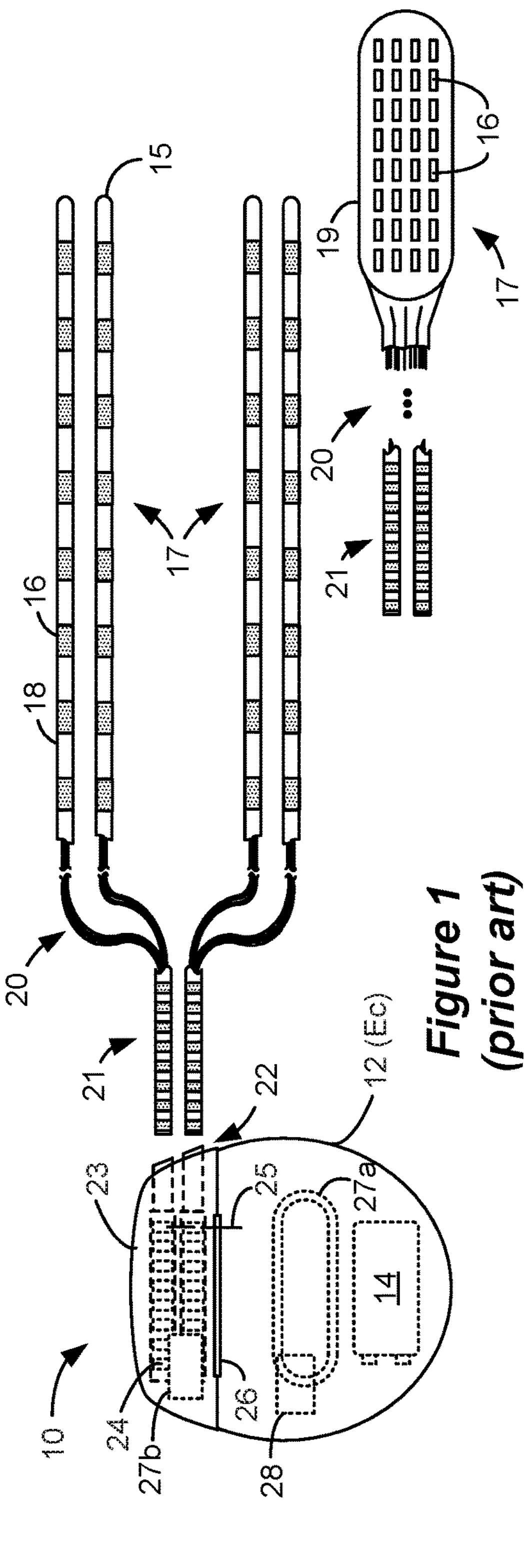
Figure 1 (prior art)
FIG. 1 shows an Implantable Pulse Generator (IPG), in accordance with the prior art.
Figure 2A:
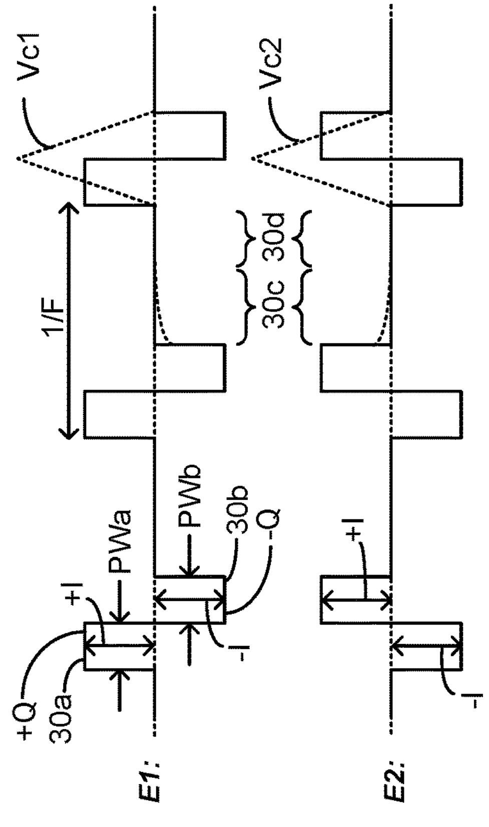
Figure 2A (prior art)
FIGS. 2A and 2B show an example of stimulation pulses producible by the IPG, in accordance with the prior art.
Figure 2B:
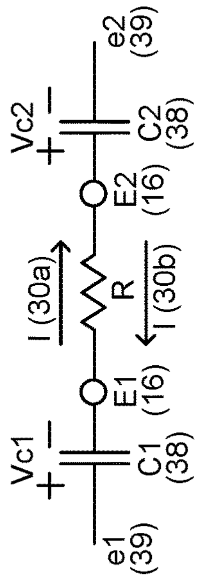
Figure 2B (prior art)

As noted, the goal of DC offset compensation circuitry 150 is to remove any differences in the DC voltages at the inputs to the sense amp circuitry 110. This DC offset is denoted by voltage Voff in FIG. 7, which may be positive or negative depending whether the voltage at X+ is higher or lower than the voltage at X−. DC offset Voff may result at least in part from differences to which the DC-blocking capacitors 38 at the electrode nodes 39 input to the diff amp 130 are charged, as represented by Vs+ and Vs−, which again may be positive or negative. Ideally, the DC-blocking capacitors 38 would not be charged, and hence Vs+ and Vs− would equal zero, in particular because charge recovery mechanisms operating within the IPG 100 would be expected to remove stored charge. In this regard, and as explained earlier (see FIGS. 2A & 2B), stimulation can be provided using biphasic pulses, with second pulse phases 30*b* actively recovering charge stored on capacitive structures injected during a first pulse phase 30*a*. Additionally or alternatively, passive charge recovery can be employed during periods 30*c* to recover any remaining charge stored on capacitive components.

Nevertheless, such charge recovery mechanisms may not be perfect. For example, due to non-idealities in the circuitry, the charge of the phases 30*a* and 30*b* of a biphasic pulse may not be perfectly charge balanced, despite programming the stimulation circuitry 28 to provide charge-balanced phases. Further, there may be slight differences in the capacitance values of the DC-blocking capacitors 38 which would tend to imbalance the charges stored on them. Thus, aresidual charge (voltage) imbalance may remain at the inputs to the sense amp circuitry 110, with deleterious results. Even a seemingly small DC offset (e.g., Voff=0.01 V) would produce a large DC offset in the differential output D+/D− of the diff amp 130 (e.g., 2V for a gain G of 200). Excessive DC amplification may also cause the differential output D+/D− to become saturated and pinned to the diff amp's power supply voltage (VH, Vdd, etc.) or to ground. Furthermore, excessive DC amplification may cause high or low saturation in the ADC 112, as discussed further below with respect to FIG. 8. In either case, the sense amp circuitry 100 and/or the ADC 112 will not function properly to resolve the AC small signals (e.g., neural responses) of interest.

Even if the DC-blocking capacitors 38 are completely discharged (e.g., Vs+=Vs−=0) or are otherwise completely balanced (Vs+=Vs−), other mechanisms may cause an inherent imbalance at the inputs X+ and X− to the sense amp circuitry 110. For example, the diff amp 130 in the sense amp circuitry 110 may not be ideal, and may have an inherent DC offset at input inputs X+ and X−. Electrochemical effects at the interface between the electrodes 16 and the tissue can also induce a small DC voltage offset at the inputs to the sense amp circuitry 110, particularly if the electrodes 16 input to the sense amp circuitry have different areas or compositions. Still further, a DC-blocking capacitor 38 may not be present at every potential sensing electrode, and therefore uneven charging of these capacitors may not be responsible for causing a DC offset. Although not shown, some sensing electrodes may have a large resistors in parallel with their DC-blocking capacitors, such as at the case electrode (Ec), as explained in the above-referenced '202 patent.

Regardless of the reason the inputs X+ and X− may be DC imbalanced (Voff is not zero), the goal of DC offset compensation circuitry 150 is to reduce or eliminate this DC imbalance to encourage Voff to zero, or closer to zero, so that AC tissue signals can be more reliably sensed. This is accomplished in the example shown in FIG. 7 by having DC offset compensation 150 assess the DC offset, and convert this offset to a current Idc that is used to adjust the voltage across one of the DC-blocking capacitors 38—in this example, Vs+ across the DC-blocking capacitor in series with input X+. In other words, the goal of circuitry 150 is to adjust Vs+ via current Idc until Voff equals or approaches zero. This would likely set Vs+ equal to Vs−, especially if different charges on the DC-blocking blocking capacitors 38 are solely response for the DC offset Voff. Although not shown, note that current Idc could also be provided to the other input X− to adjust Vs− towards Vs+. Note that Vs+ and Vs− may be referenced to a common mode voltage in the tissue, Vcm, which comprises a current return for Idc. Vcm may be inherent in the tissue, or established by the IPG as explained earlier with reference to the above-incorporated '202 patent and '443 Publication.

Preferably, Idc is on the order of microAmps, which is very small in comparison to the magnitude of the stimulation currents provided to the electrodes (typically milliAmps) by the stimulation circuitry 28. In this respect, Idc does not appreciably contribute to stimulation of the patient's tissue. Idc may be positive (which will increase Vs+) or negative (which will decrease Vs+), as explained further below.

The DC offset compensation circuitry 150 receives an input 158 indicative of the DC offset Voff, and in the example of FIG. 7 this input comprises the differential analog output D+/D− from the diff amp 130. This output comprises an amplified version of the DC offset Voff. However, other representations of DC offset Voff can be received by the DC offset compensation circuitry 150 at input 158, such as other differential outputs present along analog processing circuitry 140 at blocks 142, 144, 146, or 148. Use of these other outputs may be preferred because they are filtered and/or impart different gains to the DC offset Voff. The DC offset compensation circuitry 150 could also receive Voff directly as an input 158 (at X+/X−), although this is less preferred because Voff is normally relatively small.

An example of circuitry useable for the DC offset compensation circuitry 150 is shown in FIG. 7. Because this circuitry is explained in detail in the above-incorporated '273 Publication, it is only briefly described here. A bias current (Ibias) forms currents (I1 and I2) through two inputs legs which respectively receive the analog outputs D+ and D−. These currents I1 and I2 will scale with the magnitude D− and D+ respectively. Currents I1 and I2 are reflected through a number of current mirrors, which eventually produces an output Idc=½(M/N)(I1−I2), with M and N representing scalars set in the certain of the current mirrors. Scalars M and N can be programmed in accordance with gain control signals Gdc.

Operation of DC offset compensation circuitry 150 can be understood by considering different values for Voff. If Voff is zero, the DC voltages at X+ and X− are equal (presumably because Vs+ is equal to Vs−). After amplification by the diff amp 130, the DC voltages of D+ and D− would also be equal, meaning I1=I2, which causes Idc to equal zero. This leaves the DC-blocking capacitor 38 at input X+ unaffected—i.e., it is not charged or discharged—and Vs+ remains unaffected.

If Voff is positive, the DC voltage at X+ is higher than at X− (presumably because Vs+ is larger than Vs−). After amplification (130), the DC voltage of D+ would be higher than at D−. This results in I2 being higher than I1, which causes Idc to be negative. This negative current Idc will discharge the DC-blocking capacitor 38 at input X+, which will decrease Vs+ (towards Vs−) and bring Voff towards zero.

If Voff is negative, this means that the DC voltage at X+ is lower than at X− (presumably because Vs+ is smaller than Vs−). After amplification (130), the DC voltage of D+ would be lower than at D−. This results in I2 being lower than I1, which causes Idc to be positive. This positive current Idc will charge the DC-blocking capacitor 38 at input X+, which will increase Vs+ (towards Vs−) and bring Voff towards zero.

In short, as the DC offset compensation circuitry 150 operates, feedback will eventually set DC offset Voff equal to or closer to zero by charging or discharging the DC blocking capacitor 38 coupled to input X+, presumably to a level where Vs+ equals Vs−. The DC offset compensation circuitry 150 can operate whether differential or single ended sensing is used. The speed with which DC offset compensation occurs—i.e., the speed at which Voff is set to zero—is strongly influenced by the magnitude of Idc, which can be set by gain control signals Gdc.

Figure 8:
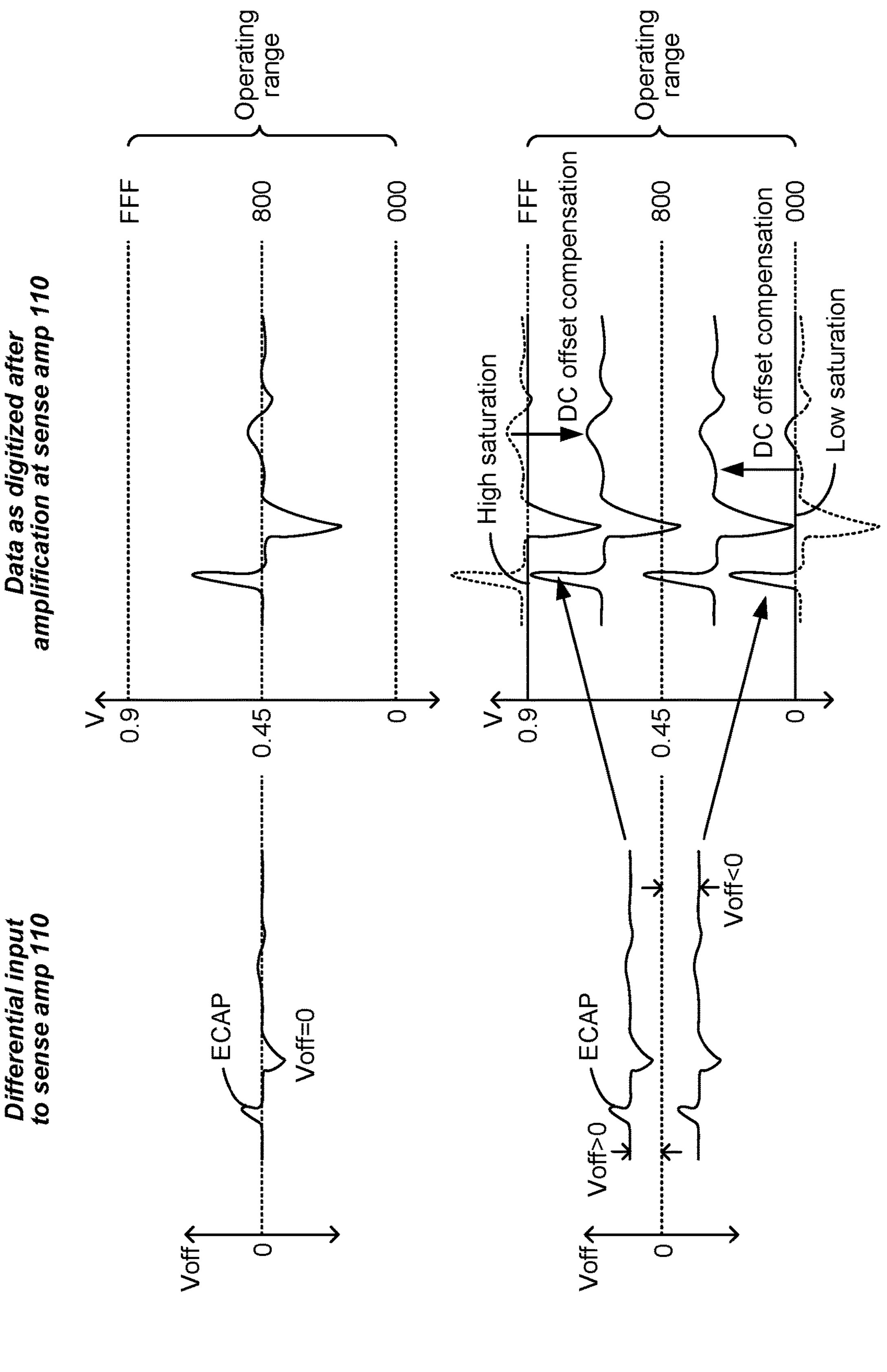
FIG. 8 shows how a DC offset can cause saturation of digitized waveforms of a tissue signal, and how DC offset compensation mitigates this.

FIG. 8 shows how a DC offset Voff at the input to the sense amp circuitry 110 can affect sensing, and how the DC offset can be rectified by use of the DC offset compensation circuitry 150. The top shows the sensing of a tissue signal, such as an ECAP neural response, in the situation where the DC offset Voff is zero. As explained above, this neural response will be amplified by the sense amp circuitry 110 and presented to the ADC 112 where it is digitized. In this example, it is assumed that the ADC 112 is a 12-bit ADC and thus will assign a digital value of 000 to FFF (in hexadecimal, or 000000000000 to 111111111111 in binary) to each of the voltage values in the amplified neural response, in accordance with the sampling rate of the ADC. This defines an operating range for the ADC 112, which may be from 0.0 V (000) to 0.9V (FFF) in one example. Because Voff is equal to 0 at the top of the FIG. 8, it can be seen that the amplified and digitized neural response fits within the operating range, and is roughly centered around the midpoint (0.45V or 800 in hexadecimal) of that range. As such, the neural response is validly sensed by the ADC 112, and thus the neural response algorithm 124 may consider this response.

The bottom of FIG. 8 shows the sensing of a neural response in the situation where the DC offset Voff is not zero, which may result in high or low saturation of the digitized neural response in the ADC 112. As noted above, when Voff>0, the differential output of the sense amp circuitry 110 may be pinned to a power supply voltage. Alternatively, even if the sense amp circuitry 110's can properly sense the neural response, that response may exceed the maximum of the operating range of the ADC 112 (0.9V or FFF). In either case, the ADC 112 clips the sensed neural response, such that a significant number of higher voltages in the digitized neural response are clipped to the maximum of the operating range of the ADC 112 (0.9V or FFF) as shown in FIG. 8, resulting in high saturation in the ADC 112. The neural response algorithm 124 can assess this digitized response, and upon determining the presence of one or more maximum digital values may conclude that high saturation has occurred, and that this digitized response should be rejected as invalid.

Likewise, when Voff<0, the differential output of the sense amp circuitry 110 may be pinned to ground, and/or the response may fall below the minimum of the operating range of the ADC 112 (0.0V or 000). The ADC 112 in this circumstance clips the sensed neural response, such that a significant number of lower voltages in the digitized neural response are clipped to the minimum of the operating range of the ADC 112, resulting in low saturation in the ADC 112. The neural response algorithm 124 can assess this digitized response, and upon seeing one or more minimum digital values may conclude that low saturation has occurred, and reject this digitized response as invalid.

In response to determining that either high or low saturation has occurred, the neural response algorithm 124 may: enable use of the DC offset compensation circuitry 150 (ENdc) (although the circuitry 150 may also operate independently and be enabled whenever sensing is occurring); provide gain control (Gdc) to set a general magnitude of Idc (see bus 154, FIG. 5); and control a MUX 156 (see bus 152, FIG. 5) to connect the output of the DC offset compensation circuitry 150 (Idc) to one of the two inputs (e.g., X+) that have currently been selected to act as sensing electrodes for neural sensing.

The DC offset compensation circuitry 150 can eventually correct high and low saturation conditions by setting Voff closer to 0 (ideally, to 0) at the input of the sense amp circuitry 110, and this is also shown at the bottom of FIG. 8. If high saturation occurs (Voff>0), operation of the circuitry 150 will over some time period decrease Voff closer to zero, which will decrease the voltages of the digitized samples, eventually to a point where no samples are maximized, and the entire response fits within the operating range of the ADC 112. Similarly, if low saturation occurs (Voff<0), operation of the circuitry 150 will over some time period increase Voff closer to zero, which will increase the voltages of the digitized samples, eventually to a point where no samples are minimized, and the entire response fits within the operating range of the ADC 112. As such, operation of the DC offset compensation circuitry 150 eventually renders valid sensed tissue signals, which the neural response algorithm 124 can use to determine features as necessary for proper IPG control.

Although beneficial, DC offset compensation circuitry 150 may in certain circumstances take a prohibitively long time to provide such compensation. Assume that Idc as output by this circuitry 150 is 1 μA, that the DC-blocking capacitors have a value of 4.7 μF, and that Voff is significantly high (e.g., 2V). Eliminating this voltage would require 9.4 μC of charge (Q=C*V), which would require 9.4 seconds if a 1 μA current is used (t=Q/I). This is a considerable amount of time during which tissue signal sensing may not be reliably accomplished.

Recognizing this, the inventors has devised solutions to provide DC offset compensation that do not rely solely on use of a discrete DC offset compensation circuitry such as 150 (although circuitry 150 can also be used in conjunction with the disclosed solutions). Instead, when a DC offset Voff is present at the inputs to the sense amp circuitry 110, the stimulation circuitry 28 is controlled to remove this DC offset by providing a compensation current Ix preferably comprising one or more charge imbalanced pulses that are either net cathodic (−Q) or net anodic (+Q). This compensation current Ix is preferably provided to both of the sensing electrodes, although it could also be provided to only one electrode, and potentially to neither sensing electrode. Control of the stimulation circuitry 28 to provide the compensating current can occur using a DC offset compensation algorithm 200 (FIG. 5) programmed into the IPG's control circuitry 102 and via bus 118 (FIG. 5). The DC offset compensation algorithm 200 can operate as a program within the neural response algorithm 124 (FIG. 5), or may comprise a separate program in the control circuitry 102. Use of the stimulation circuitry 28 itself to provide DC offset compensation is beneficial because such stimulation circuitry is already present in the IPG 100, and is able to provide larger amplitude currents to remove the DC offset Voff more quickly.

Figure 9A:
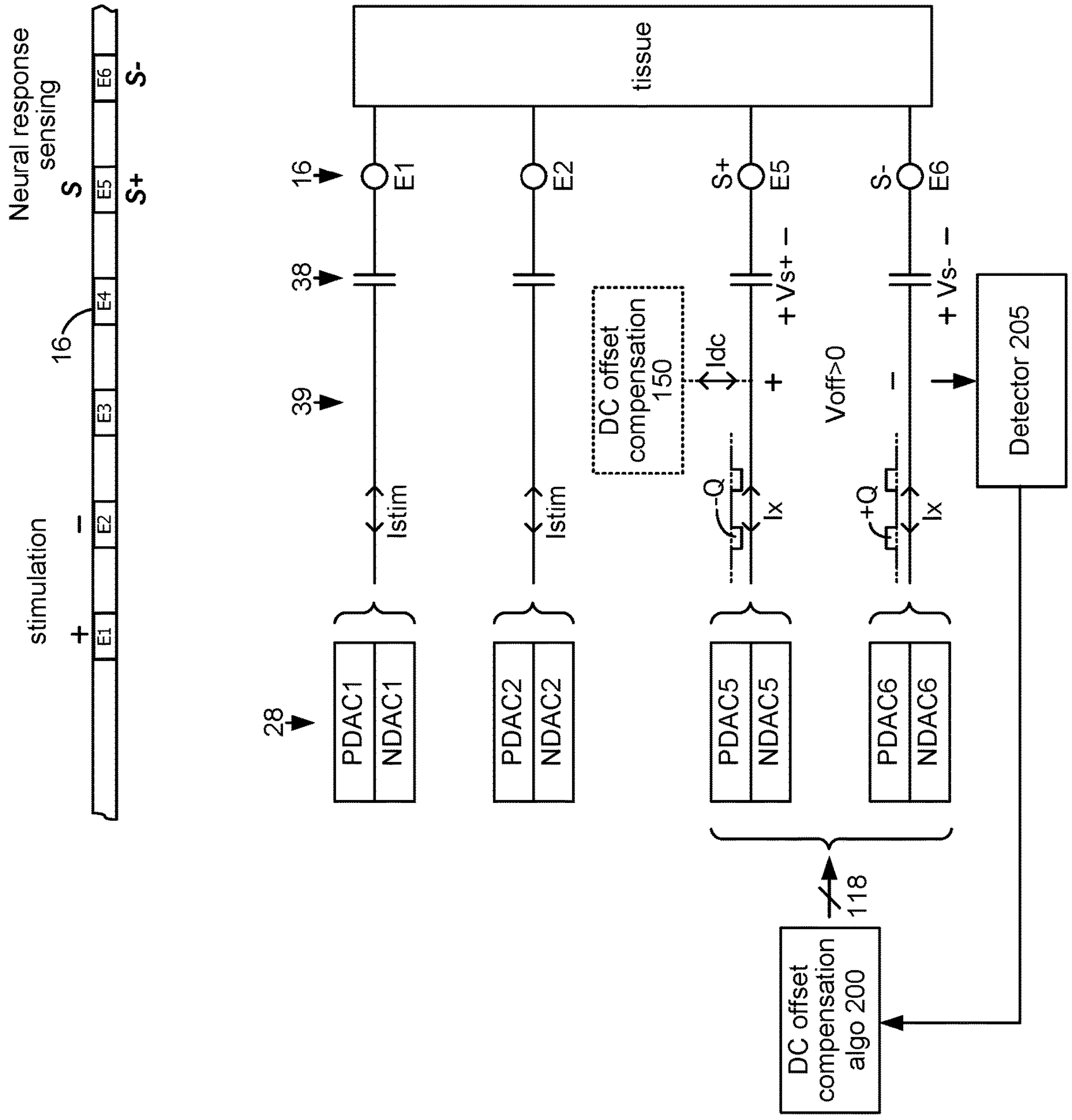
FIGS. 9A and 9B show a different approach to DC offset compensation in which the stimulation circuitry is controlled by a DC offset compensation algorithm to provide a compensating current at the sensing electrodes.

FIG. 9A shows an example of the disclosed technique at a high level. This example assumes as before (FIG. 6) that a stimulation current (Istim) is provided by the stimulation circuitry 28 at certain electrodes (E1, E2) in accordance with a stimulation program, and that a tissue signal such as a neural response will be sensed (differentially) at different electrodes (E5, E6). Istim may comprise a therapeutic stimulation current tailored to provide suitable stimulation therapy for the patient, which as noted earlier can comprise stimulation pulses with a prescribed amplitude, pulse width, frequency, etc. However, Istim can also comprise a non-therapeutic current (e.g., pulses) used specifically for the purpose of causing and measuring neural responses, which may be used in addition to therapeutic stimulation. As discussed earlier, a DC offset Voff at the inputs to the sense amp circuitry 110 may require compensation, and it was explained previously how DC offset compensation circuitry 150 could accomplish this through providing current Idc. However, DC offset compensation circuitry 150 may take too long to provide the required compensation, and so other or additional means of compensation may be necessary.

In this example, a DC offset compensation algorithm 200 provides such compensation by controlling the stimulation circuitry 28 to provide a compensating current Ix at one or both of the sensing electrodes. At a high level, detector circuitry 205 produces data indicative of the DC offset Voff between the inputs X+ and X− of the sense amp circuitry 110. This detector 205 can comprise different forms and circuitries, and may comprises part of the control circuitry 102, or may be independent from circuitry 102, as shown in the examples that follow. The detector 205 can also provide different kinds of data to the DC offset compensation algorithm 200, again as explained below. The DC offset compensation algorithm 200 in turn uses this data control the stimulation circuitry 28 to issue the compensating current Ix.

This compensating current Ix is preferably formed of one or more charge imbalanced pulses that are either net cathodic or net anodic, depending whether the DC offset Voff is positive or negative, and whether the current is provided to sensing electrode S+, S− or both. For example, in FIG. 9A it is assumed that Voff is greater than zero. To compensate, the DC offset compensation algorithm 200 can cause the stimulation circuitry 28 to issue a compensating current Ix comprising one or more net cathodic pulses at sensing electrode S+(E5) (using NDAC5). This has the effect of decreasing Vs+(e.g., eventually to the value of Vs−) and thus decreasing Voff closer to zero. Alternatively, or additionally, the DC offset compensation algorithm 200 can cause the stimulation circuitry 28 to issue an opposite-polarity compensating current Ix comprising one or more net anodic pulses at sensing electrode S− (E6) (using PDAC6).

This has the effect of increasing Vs− (e.g., eventually to the value of Vs+) and thus increasing Voff closer to zero as is desirable.

Preferably, the DC offset compensation algorithm 200 causes the stimulation circuitry 28 to issue the compensating current Ix at both of the sensing electrodes, with the opposite-polarity pulses of both currents being issued simultaneously. This is preferred for a couple of different reasons. First, Voff to approach zero more quickly, because Vs+ is decreased simultaneously with Vs− being increased. Second, providing opposite-polarity pulses at both sense electrodes provides a current return which assures that the net current flowing to the tissue is zero, thus preventing charge build-up in the tissue.

The DC offset compensation algorithm 200 would operate similarly if Voff is less than zero, but would flip the polarities described above. In this circumstance, the DC offset compensation algorithm 200 can cause the stimulation circuitry 28 to issue a compensating current Ix comprising one or more net anodic pulses at sensing electrode S+(E5) (using PDAC5), which would increase Vs+ and thus increase Voff closer to zero. And/or, the DC offset compensation algorithm 200 can cause the stimulation circuitry 28 to issue an opposite-polarity compensating current Ix comprising one or more net cathodic pulses at sensing electrode S− (E6) (using NDAC6), which would decrease Vs− and thus increase Voff closer to zero.

While preferred that the stimulation circuitry 28 be controlled to provide the compensating current Ix to both sensing electrodes, DC offset compensation can occur if only one of the sensing electrodes is provided a current. For example, compensating current Ix can be provided to either S+(E5) or S− (E6), with an opposite-polarity current return provided to any other electrodes (E7, E8, etc.) or to the case electrode (Ec). Alternatively, a current return for the compensating current Ix can occur by provided by a voltage (e.g., Vcm, Vref) at any of the electrodes. Still further, the compensation algorithm 200 may also issue the compensating current at neither of the sensing electrodes, in the circumstance where there is evidence of that this current would couple to the sensing electrodes in a manner that would provide DC offset compensation. For example, internal or external leakage conduction paths may allow a compensating current Ix to be provided at nodes different from the sensing electrodes to address an imbalance at the sensing electrodes, without delivering that compensating current to either of the sensing electrodes directly.

Although not shown or discussed further, DC offset compensation algorithm 200 can also be used during single-ended sensing to bring a single sensing electrode S to a suitable DC value relative to Vref, in which case the stimulation circuitry 28 is driven with a compensative current Ix at electrode S, with a current return acting in any of the ways previously discussed.

Figure 9B:
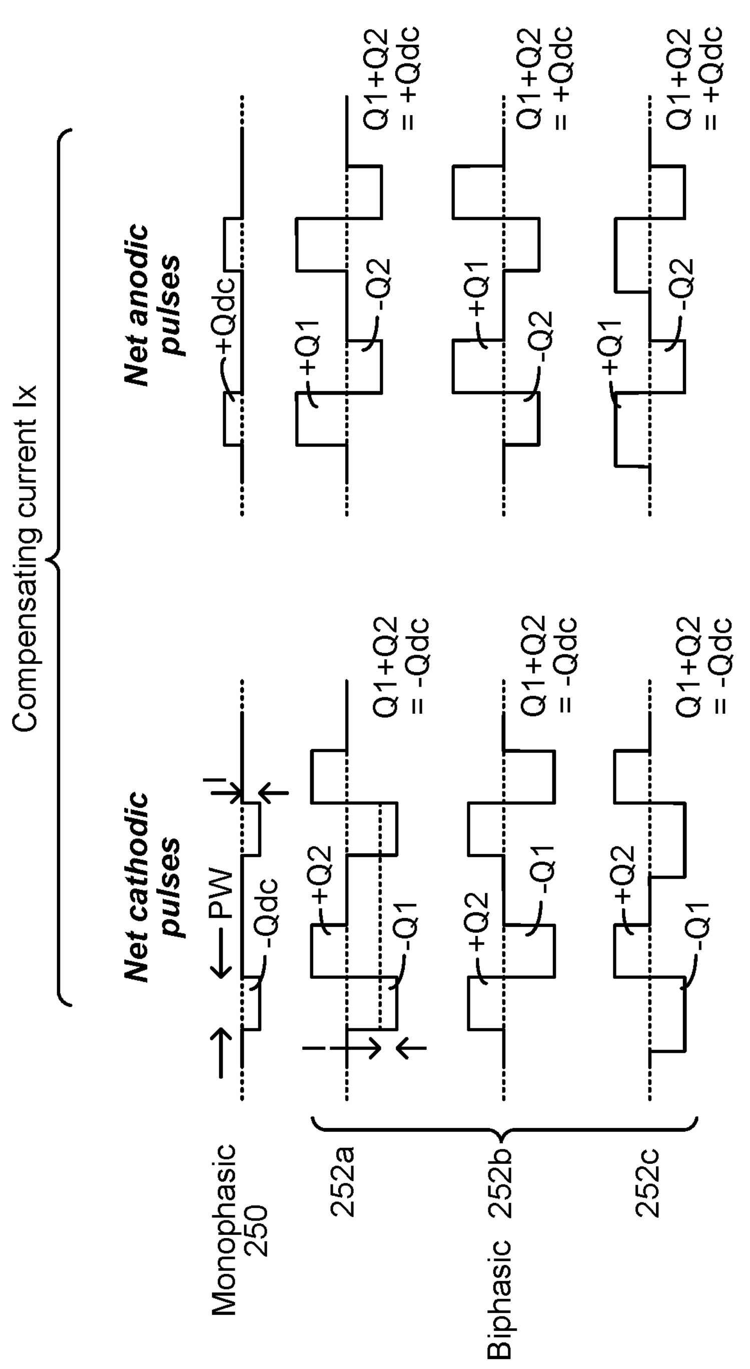

Examples of charge-imbalanced pulses the DC offset compensation algorithm 200 can cause the stimulation circuitry 28 to issue are shown in FIG. 9B. Each of the pulses illustrated have a net charge of either −Qdc (net cathodic pulses) or +Qdc (net anodic pulses) depending on the polarity of currents used to produce them. Pulses 250 are monophasic having only a single cathodic or anodic phase, in which Qdc is defined at the product of the pulse width (PW) and the current (I).

The pulses can also comprise charge-imbalanced biphasic pulses. For example, biphasic pulses 252*a* and 252*b* have two phases with the same pulse width, PW, but with different amplitudes. For example, the net cathodic pulses have a cathodic phase (−Q1) with a larger amplitude than the anodic phase (+Q2, with the two phases differing by amplitude I), with the cathodic phases either occurring first (252*a*) or last (252*b*), resulting in a net cathodic charge of −Qdc. The net anodic pulses have an anodic phase (+Q1) with a larger amplitude than the cathodic phase (−Q2, again, differing by I), with the anodic phases either occurring first (252*a*) or last (252*b*), resulting in a net anodic charge of +Qdc. The biphasic pulses 252*c* have phases with the same current amplitude, but with different pulse widths, with the net cathodic pulses having a longer cathodic phase (−Q1), and with the net anodic pulses having a longer anodic phase (+Q1), which again results in net cathodic and anodic charges of −Qdc and +Qdc equal to the amplitude times the difference in the pulse widths of the phases. These are just some examples of charge imbalanced pulses having a net charge that the algorithm 200 can cause the stimulation circuitry to produce to provide DC offset compensation. One skilled will recognize that other pulses of odd shapes and/or different numbers of phases (e.g., more than two) are possible, and such approaches may comprise a combination, superposition, or summation of multiple monophasic or biphasic pulses.

Figure 10A:
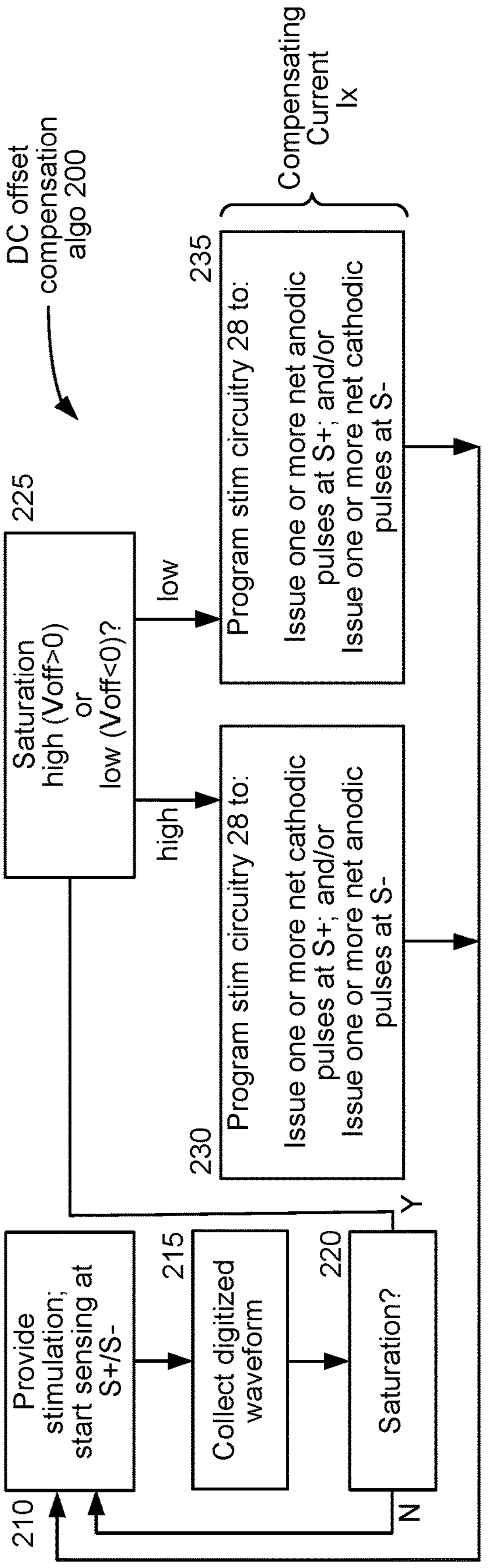

FIG. 10A shows high level details the DC offset compensation algorithm 200 in one example. As is true for all examples of the DC offset compensation algorithm 200 disclosed herein, one skilled in the art will understand that the order of steps could be varied, that additional steps could be added, or that certain steps can be removed.

Stimulation is provided at the selected stimulation electrodes (e.g., E1 and E2), and tissue signal (e.g., neural response) sensing starts at the selected sensing electrodes (E5/E6, S+/S−) (210). The ADC 112 samples the tissue signal, and the resulting digitized waveform is provided to the neural response algorithm 124, which as noted earlier will be used to assess the tissue signal.

Figure 10B:
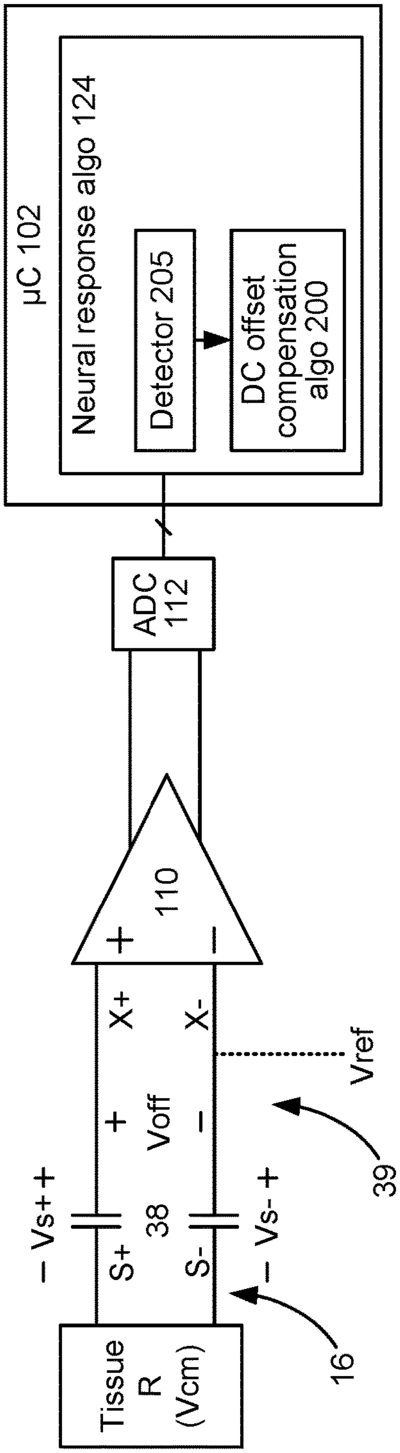
FIG. 10B shows a detector useable with the algorithm.

Algorithm 200 next determines whether the digitized waveform is saturated (220), which requires use of the detector 205. In this example, and as shown in FIG. 10B, the detector 205 comprises a program within the neural response algorithm 124 (or the DC offset compensation algorithm 200) which assesses the digitized waveform and determines whether one or more digital samples in the digitized waveforms, or some significant number of samples, is at maximum (FFF) or minimum (000) values. The neural response algorithm 124 may also independently of algorithm 200 use saturation information as provided by the detector 205 to determine whether a particular sampled tissue signal is valid, as discussed above. If no saturation has occurred, stimulation and sensing can continue if necessary (210). In this regard, note that sensing a tissue signal such as a neural response may involve several iterations of stimulation and sensing, with the neural response algorithm 124 processing or averaging the digitized waveforms to reduce noise or enhance signal resolution.

If saturation is present (220), the algorithm 200 assesses whether such saturation is high or low, which will depend on whether the saturated samples are maximized (FFF) or minimized (000) (225), and in either case causes the stimulation circuitry 28 to issue a compensating current Ix at at least one of the sensing electrodes. One skilled will realize steps 220 and 225 may be combined.

If saturation is high, this implies that the DC offset Voff is greater than zero, as explained earlier with reference to FIG. 8. The algorithm 200 will cause the stimulation circuitry 28 to issue a compensating current Ix of one or more net cathodic pulses at S+, and/or one or more net anodic pulses at S− (230), which decreases Vs+ and increases Vs− respectively, thus decreasing Voff closer to zero as discussed earlier. If saturation is low, this implies that the DC offset Voff is less than zero, and thus the stimulation circuitry will be controlled to issue a compensating current Ix of the opposite polarity. In this case, the algorithm 200 will cause the stimulation circuitry 28 to issue one or more net anodic pulses at S+, and/or one or more net cathodic pulses at S− (235), which increase Vs+ and decreases Vs− respectively, thus increasing Voff closer to zero as discussed earlier. Note that the compensating current Ix at steps 230 and 235 may be controlled separate from other tasks, such as delivering the stimulation current (Istim, FIG. 9A) that invokes the neural responses (e.g., ECAPs) being sensed. In this regard, the stimulation current Istim and the compensating current Ix may be issued in separate timing channels in the stimulation circuitry 28.

Once the algorithm 200 has issued the appropriate compensating current Ix, the algorithm 200 can iterate by once again stimulating and sensing (210); collecting a new digitized waveform (215); and assessing whether saturation is present in this new digitized waveform (220). If compensation previously provided at steps 230 or 235 has not sufficiently corrected the DC offset Voff and saturation is still present (220), the algorithm can again provide the necessary compensating current Ix at one or both sensing electrodes (230, 235) to move Voff even closer to zero. After some number of iterations, Voff would be brought close enough to zero that the digitized waveform is brought within the operating range of the ADC 112 and is no longer clipped, at which point the algorithm 200 would stop providing the compensating current Ix. In this respect, the algorithm 200 via control of the stimulation circuitry 28 acts similarly to the DC offset compensation circuitry 150 described earlier, and as illustrated in FIG. 8.

The extent to which DC offset Voff is brought closer to zero through use of the DC offset compensation algorithm 200 of FIG. 10 depends on the net charge, Qdc of the issued pulse(s) at steps 230 and 235. Assuming the DC-blocking capacitors have a capacitance of 4.7 μF, each charge imbalanced pulse would change the voltages across these capacitors by Qdc/4.7 μF ($\Delta V=\Delta Q/C$), which depends on the values of PW and I chosen to form the charge imbalanced pulses (Qdc).

Note that it is not strictly necessary to determine at steps 220 and 225 whether the digitized waveform is saturated, as discussed earlier with reference to FIG. 8. Instead, the algorithm 200 may simply determine at these steps that values in the digitized waveform are too high (and at risk of high saturation), or too low (and at risk of low saturation). In these cases, because the offset is larger than desired, even though not waveform is not technically saturated, a compensating current can issue at steps 230 or 235 to better center the digitize waveform within the operating range of the ADC 112.

Figure 11:
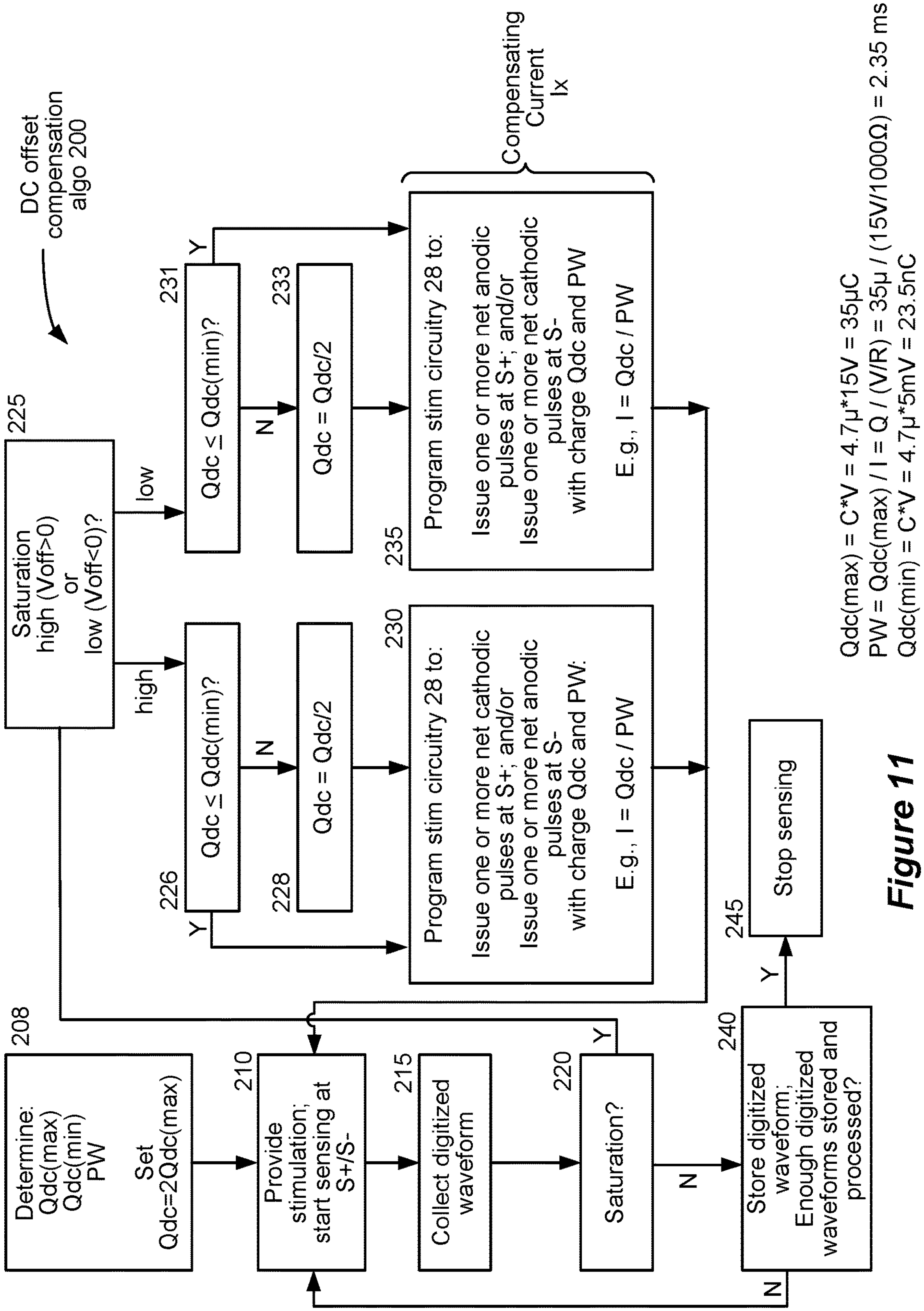
FIG. 11 shows a more-detailed second example of a DC offset compensation algorithm.

FIG. 11 shows another example of the DC offset compensation algorithm 200 that further assists in setting parameters of the compensating current Ix to logical values, and to gradually decreasing Qdc upon each iteration to remove DC offset Voff in a more controlled manner. Similar steps discussed in the example of FIG. 10 are denoted with the same element numbers.

The algorithm 200 begins by determining or setting certain parameters that will be used to define the compensative current Ix and its charge imbalanced pulses (208). First, a maximum Qdc, Qdc(max), is determined, which will be used initially to adjust the DC offset, but which will also be gradually decreased as the algorithm 200 iterates. Qdc (max) can be determined or set in different ways, but the example shown is set based on the capacitance of the DC blocking capacitors 38 (e.g., 4.7 μF) and the compliance voltage VH that powers the stimulation circuitry. In one example, this maximum voltage is 15V, but may be lower depending on the stimulation (as noted above, the compliance voltage VH is variable). Thus, assuming the compliance voltage VH is 15V, Qdc(max)=C*V=4.7 μF*15V=35 μC. A starting Qdc for the algorithm 200 can also be set at step 208 using Qdc(max), and in the depicted example, Qdc is set to 2*(Qdc(max)).

Another parameter determinable at step 208 is a minimum Qdc, Qdc(min). Qdc(min) can be determined based on the capacitance of the DC blocking capacitors 38 (e.g., 4.7 μA), as well by considering the maximum input voltage range permissible at the inputs X+/X− to the sense amplifier circuitry 110, which in one example may be 10 mV. Preferably, Qdc(min) is set to achieve a smaller increment within this range, such as half of the range (e.g., 5 mV), but even smaller fractions of the range can be used. Thus, Qdc(min) =C*V=4.7 μF*5 mV=23.5 nC. Qdc(min) denotes a minimum amount of charge used for DC offset compensation as the algorithm 200 iterates, as explained further below.

Still another parameter determinable at step 208 is a pulse width (PW) of the pulses comprising the compensating current Ix. This may be set based on the measured or estimated impedance of the tissue between the sensing electrodes (e.g., 1000Ω), the compliance voltage VH, and Qdc(max). From these parameters, pulse PW can be set to PW=Qdc(max)/I=Qdc(max)/(V/R)=35 μC/(15V/1000Ω) =2.35 ms. This pulse width PW will be used to provide a single pulse at each iteration of the algorithm 200 in this example, but this is not strictly necessary. Instead, a number of pulses may also be used at each iteration, such as 10 pulses each having a pulse width of 0.235 ms, to achieve the same effect.

Step 208 should be understood as just one way that parameters for the compensating current Ix can be determined, and parameters may be determined or set in other manners.

Stimulation and sensing are started (210), or at least sensing is started as stimulation may have already begun. The ADC 112 samples the sensed tissue signal, with the algorithm 200 collecting the digitized waveform (215). Algorithm 200 next determines whether the digitized waveform is saturated (220), and in particular whether such saturation is high or low (225). These steps were described above with reference to FIG. 10.

If a high saturation condition exists (Voff>0), the algorithm 200 inquires whether Qdc is current less than or equal to Qdc(min) (226). This condition would not be meet initially when Qdc=2Qdc(max), and so Qdc is halved (228), which sets Qdc=Qdc(max). At step 230, the algorithm 200 issues a compensating current Ix, and more specifically causes the stimulation circuitry 28 to issue one or more charge imbalances pulses to decrease Voff. Here it is assumed that a single charge-imbalanced pulse will issue with the pulse width determined earlier (PW) and the current charge value of Qdc, in the form of a net cathodic pulse at sensing electrode S+ and a net anodic pulse at sensing electrode S−. These pulses can be monophasic, or biphasic as described earlier (see FIG. 9B). The amplitude of the pulse I (or the difference in the amplitude of the phases if a biphasic pulse is used) can be determined by dividing Qdc by the pulse width as shown. As explained earlier, this will decrease Voff (possibly below zero).

If a low saturation condition exists (Voff<0), the algorithm 200 essentially completes the same steps to issue a compensating current Ix, but with the opposite polarity. Compare steps 226, 228, and 230 with steps 231, 233, and 235. As explained earlier, this will increase Voff (possibly above zero).

After issue the compensating current Ix (230, 235), the algorithm 200 can iterate by providing stimulation and sensing (210), and collecting a new digitized waveform of the sensed response (215). If saturation is still present (220), the algorithm can again issue another compensating current Ix. Assuming that Qdc is not currently equal to or less than Qdc(min) (226, 231), Qdc is again halved (228, 233), and applied to the sensing electrode(s) with the desired polarity (either 230 or 235). Assuming the pulse width is not adjusted, this means I of the charge imbalanced pulses will also be halved, which would half the amount that Voff is adjusted.

As the algorithm 200 continues to iterate, eventually Qdc would eventually become small enough that it would be equal to or less than Qdc(min) (226, 231), and thus Qdc would not be adjusted lower any further. Instead, this small Qdc value is simply used to provide the compensating current Ix (230, 235), thus providing a fine adjustment to Voff compared to the coarse adjustment occurring in earlier steps.

At some point during iteration of the algorithm 200, Voff would be close enough to zero that saturation is no longer present in the digitized waveforms provided by the ADC 112. See FIG. 8. At this point, the algorithm 200 would store the digitized waveform as valid (240), and inquire whether enough digitized waveforms have been stored and/processed to allow the neural sensing algorithm 124 to interpret the sensed tissue signal. If not, further digitized waveforms can be procured and stored (210, 215, 220, 240). If so, sensing can be stopped (245). At this point, the neural sensing algorithm 124 has access to enough examples of the tissue signal to perform its analysis of that signal, and extract desired features of that signal as described above.

One skilled will understand that the algorithm 200 can be varied in certain respects. For example, while it is preferred to halve Qdc used to providing the compensating current Ix as the algorithm 200 iterates (see steps 228, 223), Qdc could also be decreased by a set value, or gradually decreased in other ways. Further, while the example of FIG. 11 gradually adjusts Qdc by decreasing the amplitude, the amplitude can be kept constant, and instead the pulse width can be decreased. In this regard, the algorithm 200 may also receive (e.g., at step 208) a maximum amplitude Imax for the compensating current Ix that is safe and comfortable for the patient.

Figure 12:
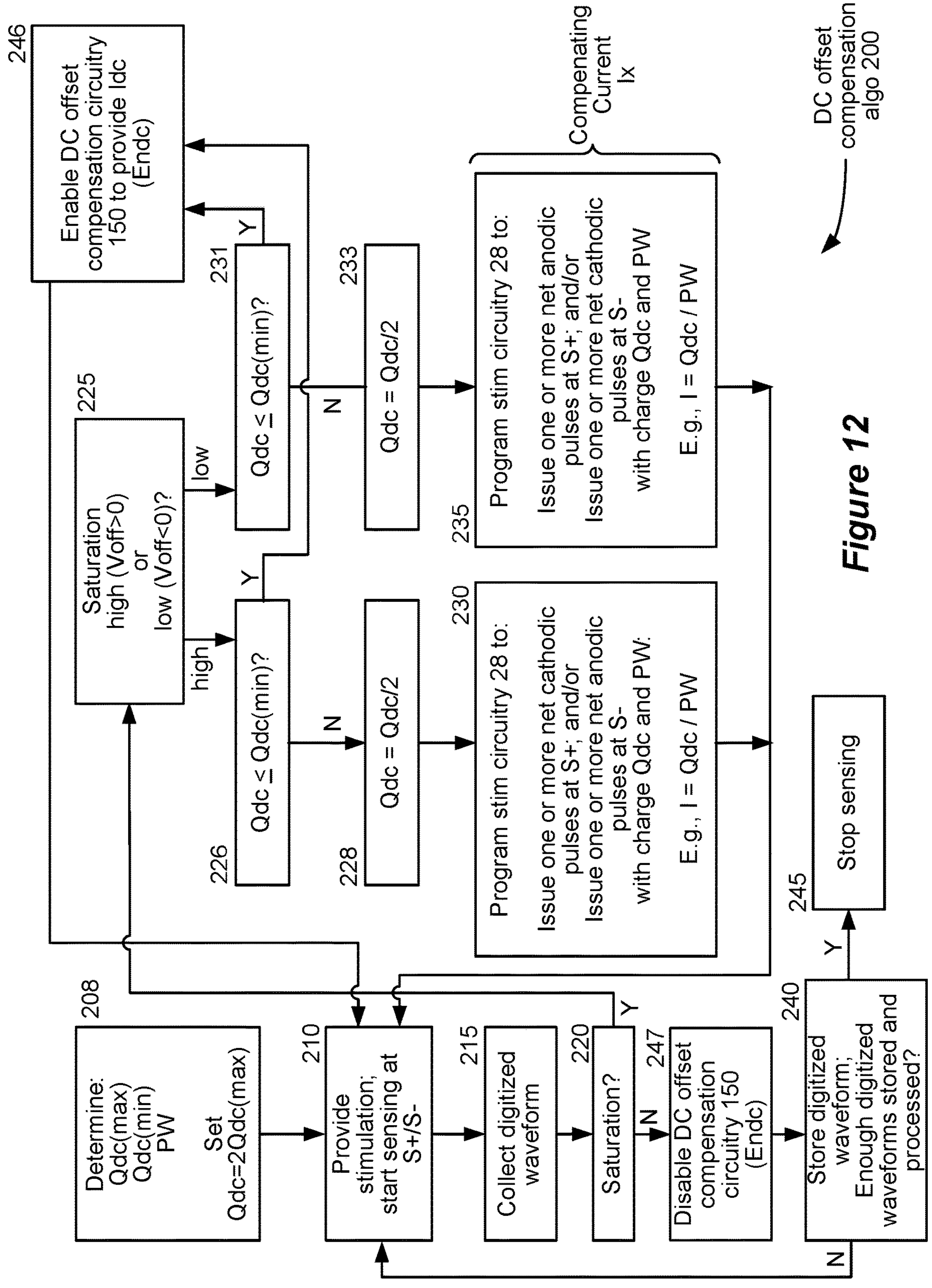
FIG. 12 shows a third example of a DC offset compensation algorithm with the stimulation circuitry controlled to provide a coarse adjustment, and with the DC offset compensation circuitry (FIG. 7) controlled to provide a fine adjustment.

FIG. 12 shows another example of the DC offset compensation algorithm 200 that employs use of the DC offset compensation circuitry 150 described earlier (FIG. 7) as well as the stimulation circuitry 28. Algorithm 200 of FIG. 12 is largely the same as the algorithm 200 of FIG. 11 in that the stimulation circuitry 28 is used to provide a compensating current Ix when the DC offset is relatively large, and when larger vales of Qdc are used to define the compensating current (230, 235). As such, the stimulation circuitry is used in this example to provide a coarse adjustment to the DC offset Voff.

However, as the algorithm 200 iterates and Qdc is gradually reduced (228, 233), the DC offset compensation circuitry 150 is thereafter used to provide Idc to provide DC offset compensation as described earlier. Specifically, at steps 226 and 231, if Qdc has been decreased to a value less than or equal to Qdc(min), the DC offset compensation circuitry 150 is enabled to provide Idc (step 246) until such time as saturation is no longer occurring (220). Thereafter, the DC offset compensation circuitry 150 can be disabled (247). Whereas the stimulation circuitry 28 is used initially to provide a coarse adjustment to the DC offset Voff, the DC offset compensation circuitry 150 later provides a fine adjustment to the DC offset Voff in this example.

Figure 13A:
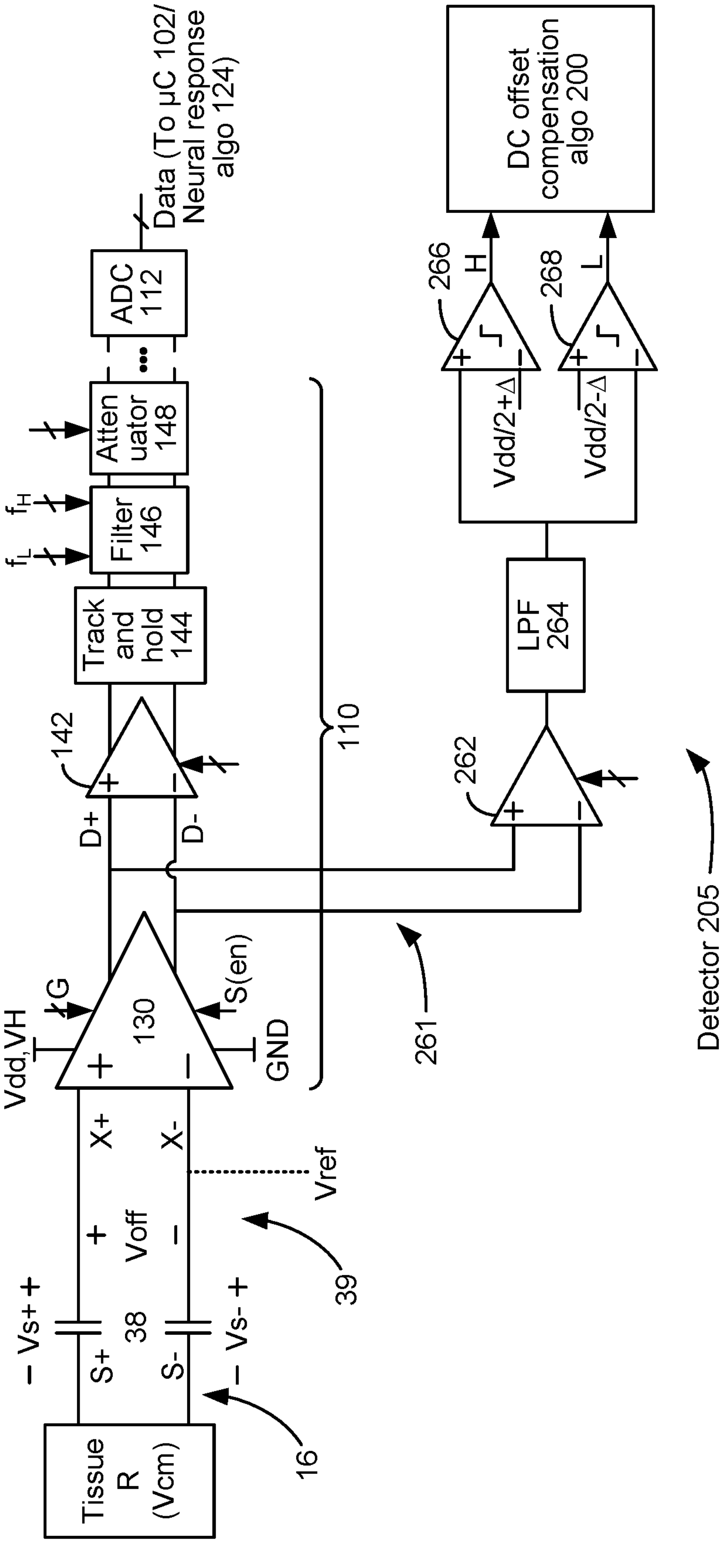
FIG. 13A shows the use of detector circuitry that provides high and low digital signals to a fourth example of a DC offset compensation algorithm of FIG. 13B.
Figure 13B:
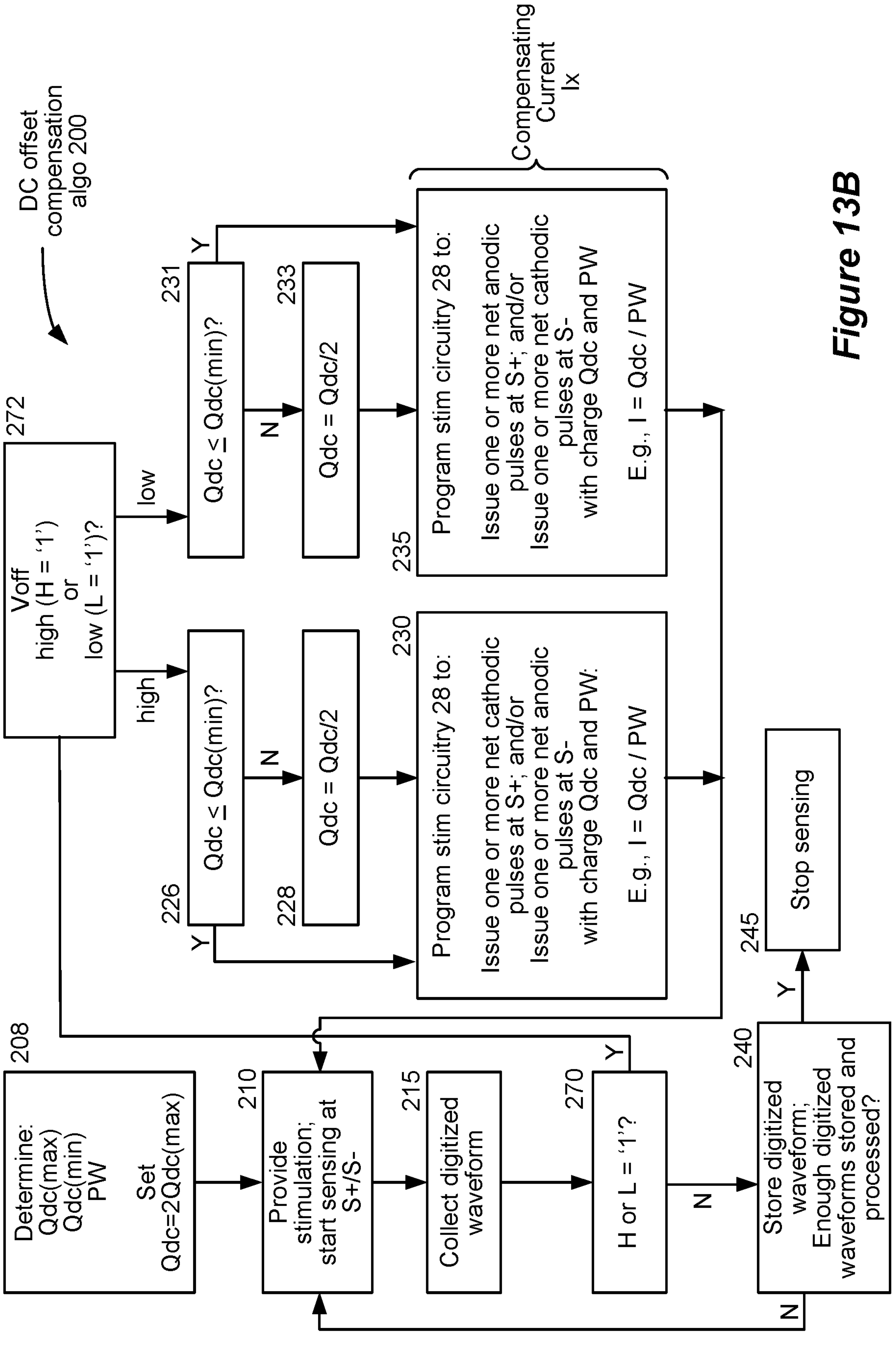

FIGS. 13A and 13B show a variation to the circuitry and the DC offset compensation algorithm 200. In this example, saturation is not determined through an assessment of the digitized waveforms provided by the ADC 112 (FIG. 8), and whether digitized values are clipped at maximum and minimum values. Instead, the detector 205 in this example comprises circuitry that assesses Voff and provides high and low digital signals H and L to the algorithm 200 that inform whether the algorithm 200 should cause a compensating current Ix to issue, and with what polarity.

In the example shown, the detector 205 comprises a diff amp 262, a low pass filter (LPF) 264, and a window comparator (266, 268) as described below. The detector 205 receives as an input 261 one or more signals indicative of DC offset Voff, such as the differential output of the diff amp 130 in the sense amp circuitry 110 as shown. However, and like the DC offset compensation circuitry 150 discussed earlier (FIG. 7), the input 261 to the detector 205 can comprise other representations of the DC offset Voff, such as other differential outputs present along analog processing circuitry 140 at blocks 142, 144, 146, or 148. The detector 205 could also receive Voff directly as an input 261 (at X+/X−).

Input 261 is provided to a diff amp 262 having a single-ended output. This single-ended output may be referenced to and centered around an output reference voltage between the power supply for the diff amp (e.g., Vdd) and ground, such as Vdd/2. Thus, the single-ended output is Vdd/2 if D+ equals D− (if Voff=0); is higher than Vdd/2 if D+ is greater than D− (if Voff>0); and is less than Vdd/2 if D+ is less than D− (if Voff<0). Both the output reference voltage and gain of diff amp 262 may be programmable. The single-ended output may be low-pass filtered at LPF 264 to remove high frequency components not reflective of the DC level of DC offset Voff.

The output of LPF 264 (if present) is provided to a window comparator comprising two comparators 266 and 268, each of which compares the output to a threshold. These thresholds may be defined relative to the output reference voltage, such as Vdd/2+Δ and Vdd/2−Δ, which are input to the comparators 266 and 268 respectively. If the output exceeds Vdd/2+Δ, meaning that Voff is significantly greater than zero, comparator 266 outputs a logical '1' at comparator output H. Likewise, if the output falls below Vdd/2−Δ, meaning that Voff is significantly less than zero, comparator 268 outputs a logical '1' at comparator output L. One skilled will understand that Δ can be set to a value at which either the diff amp 130 or the ADC 112 becomes saturated, and as such Δ is dependent on the gain provided by the sense amp circuitry 110 and the diff amp 262. Different values for Δ can be used at comparators 266 and 268 to set different thresholds. Digital outputs H and L are input to the DC offset compensation algorithm 200 in the control circuitry 102, where they are used by the algorithm 200, as explained next.

FIG. 13B shows modification to the DC offset compensation algorithm 200 when the detector 205 of FIG. 13A is used, and this modification varies from the algorithm 200 as described earlier (FIG. 11) in using digital output signals H and L to determine whether a compensating current Ix should issue, rather than by assessing saturation of the waveforms digitized by the ADC 112. Thus, at step 270, the algorithm 200 queries whether H or L has been set ('1'), with step 272 querying further whether Voff is high (H='1') or low (L='1'). (Again, steps 270 and 272 may be combined). Otherwise, the algorithm 200 may proceed as before to iteratively issue a compensating current of the correct polarity to reduce the DC offset Voff to a suitable level. Because the algorithm 200 of FIG. 13B does not require assessment of the digitized waveforms determined in the ADC 112 but instead uses digital output signals H and L, it can operate more quickly and with less computational overhead.

Various examples of the DC offset compensation algorithm 200 shown to this point involve iteration to eventually get the DC offset Voff acceptably close to zero so that sensed tissue signals are properly resolvable. In these examples, a compensating current Ix is issued by the stimulation circuitry 28 with the right polarity at each iteration, but with a charge Qdc that is not necessarily of the right magnitude to completely negate the DC offset Voff. However, the circuitry and DC offset compensation algorithm 200 of FIGS. 14A and 14B can measure DC offset Voff and compute Qdc as necessary to provide a compensating current Ix that will ideally reduce Voff to zero, without requiring the algorithm 200 to iterate.

Figure 14A:
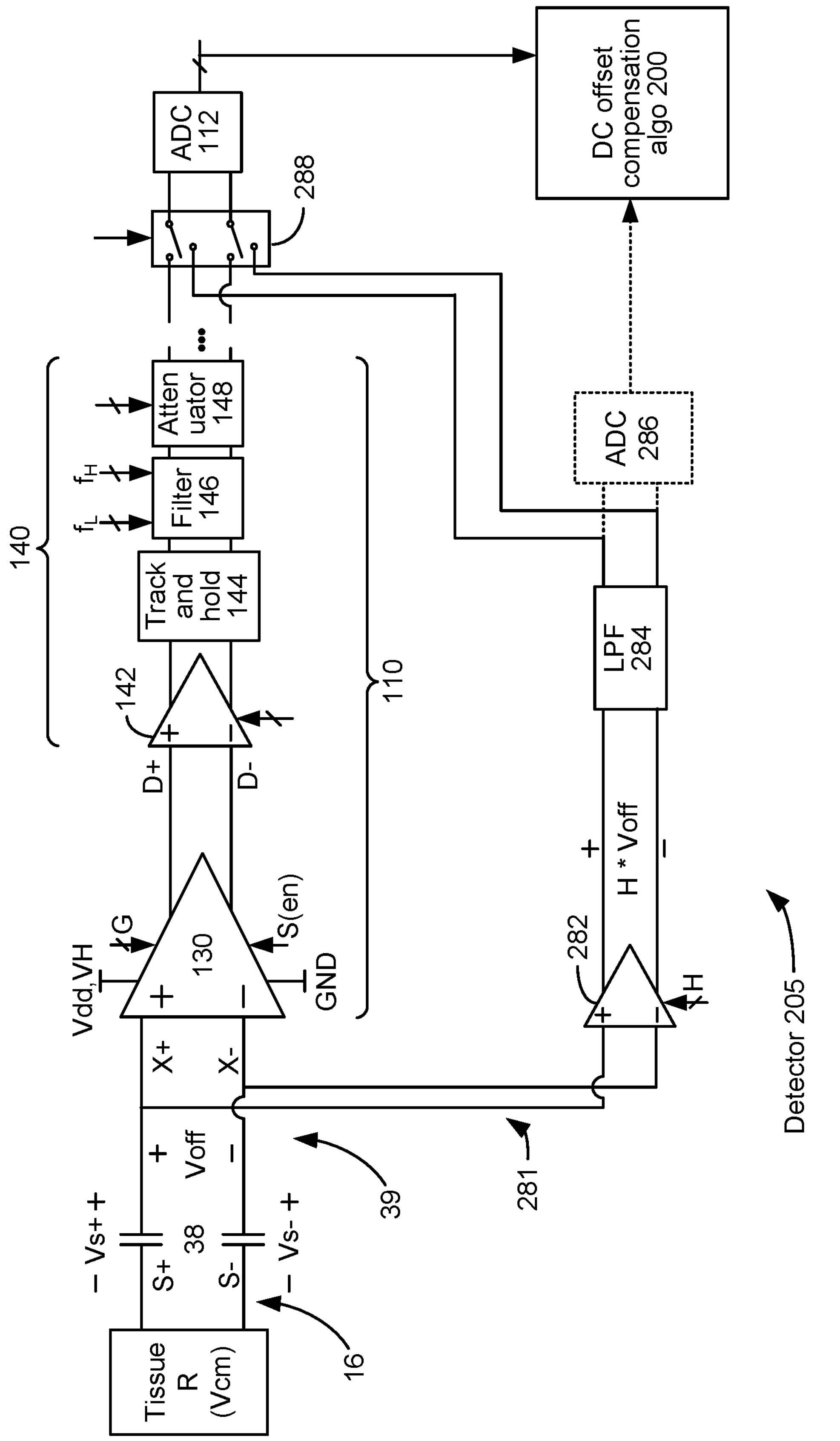
FIG. 14A shows the use of detector circuitry that provides a measurement indicative of the DC offset to a fifth example of a DC offset compensation algorithm of FIG. 14B.
Figure 14B:
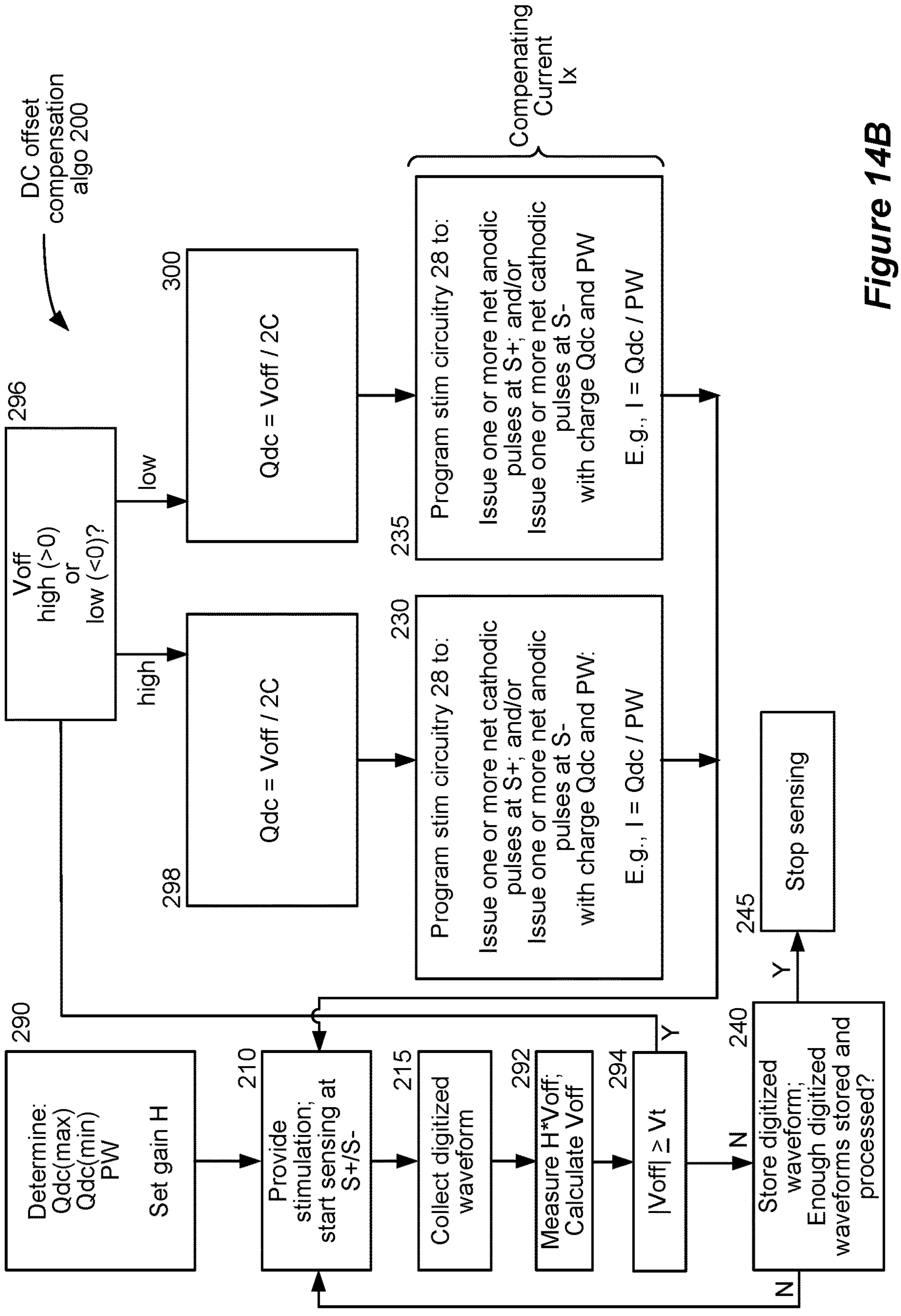

The detector 205 in the example of FIG. 14A comprises circuitry which measures Voff, or a scaled version of Voff, and reports this value to the DC offset compensation algorithm 200 (FIG. 14B). The detector 205 comprises a diff amp 282, a LPF 284, and an ADC to turn the measured value into digitals signals interpretable by the algorithm 200. An input 281 to the diff amp 282 is indicative of Voff, and preferably in this example comprises Voff as taken directly from the inputs X+/X− to the sense amp circuitry 110. However, other inputs 281 representative of Voff can be taken from the sense amp circuitry 110 as well, such as the analog outputs D+/D− or other differential outputs present along analog processing circuitry 140 at blocks 142, 144, 146, or 148. The diff amp 282 produces an output equal to H*Voff, with gain H of the diff amp 282 set to an appropriate value such that H*Voff is easily and reliably detected. In one example, H may be programmed to 10, although H can comprise other values (e.g., <1, 1, >10) depending on the circumstances. (If a gain of H=1 is indicated, diff amp 282 may not be necessary). The output H*Voff may be low pass filtered at LPF 284 to remove high frequency components not reflective of the DC level of DC offset Voff. Other circuitries or comparator designs may be used in the example of FIG. 14A.

The output of LPF 284 (if present) H*Voff is measured, and preferably this occurs using an Analog-to-Digital converter (ADC), although other circuitry could be used as well. In one example, the ADC used comprises the same ADC 112 that is used to digitize the tissue signal waveforms, and this can occur in a time-multiplexed manner using a switch 288. The switch 288 may be controlled by the algorithm 200, and can either be set to measure the output of the sense amp circuitry 110 (i.e., the tissue signal) or signal H*Voff as shown. In another example shown in dotted lines, the DC offset measurement circuitry 280 can include its own dedicated ADC 286 specifically to measure H*Voff. While this alternative requires an extra component, use of ADC 286 alleviates the need for a switch 288 and for time-multiplexed use of the ADC 112, which instead can be used solely for tissue signal detection. Regardless of the circuitry used, H*Voff is ultimately reported to the DC offset compensation algorithm 200 in digital form.

FIG. 14B shows modification to the DC offset compensation algorithm 200 when the detector 205 of FIG. 14A is used. Step 290, like step 208 described earlier, allows certain useful variables (Qdc(max), Qdc(min), PW) to be determined or set. Additionally, the algorithm 200 in this example receives or sets the gain H to be used by the diff amp 282 in detector 205. Unlike step 208, the algorithm 200 in this example does not pre-compute a charge Qdc to be used in the first iteration of the algorithm 200. Instead, as discussed further below, Qdc is computed as a function of the voltage measured by the detector 205.

Stimulation and sensing are started (210), and a digitized waveform of the tissue signal is collected from the ADC 112 (215). Next, H*Voff is measured using the detector 205 (292). If a dedicated ADC 286 is used this may occur at the same time that the digitized waveform is collected (215). If ADC 112 is used, the digitized waveform can first be collected by the ADC 112, with the switch 288 then controlled by the algorithm 200 to measure H*Voff later (when stimulation is provided again). Once H*Voff is measured, the algorithm 200 then determines Voff by dividing the result by gain H (292), which as noted above is already known to the algorithm 200 (290). If H*Voff as measured has other gains added to it as well (e.g., from gain G of the diff amp), such additional gains may also be normalized out to render Voff.

Next, the algorithm 200 compares the absolute value of Voff to a threshold Vt (294). This threshold Vt is set to a minimum value at which DC offset compensation is needed, such that a compensation current Ix will be provided if |Voff| is greater than or equal to Vt. Note that Vt can be set by considering what value for Voff will cause saturation in the sense amp circuitry 110 or in the ADC 112 (FIG. 8). In this regard, Vt may be set by considering the maximum input voltage range permissible at the inputs X+/X− to the sense amplifier circuitry 110, which in one example may be 10 mV. Vt may be set to some fraction of this range (e.g., 5 mV) to provide some guardband. One skilled in the art will realize that H*Voff as measured can also be compared to a threshold at step 294, with the threshold scaled by gain H as necessary.

If |Voff| equal or exceeds this threshold Vt (294), the algorithm 200 next considers whether Voff is too high (>0) or too low (<0) (296). (Again, steps 294 and 296 can be combined). In next steps, a charge Qdc necessary to compensate for Voff is calculated (298, 300), which requires consideration of the capacitance involved at the sensing electrodes that will receive the compensation current Ix in next steps (230, 235). If it is assumed that both sensing electrodes S+ and S− will receive the compensating current Ix, and that both electrodes have a DC-blocking capacitor 38 of capacitance C, then Qdc is computed as Voff/2C. This charge Qdc when provided at each sensing electrode via the compensating current Ix will decrease the higher-voltage input by ½Voff, and will increase the lower-voltage input by ½Voff. In sum total, this should reduce Voff to zero.

Next steps 230 and 235 provide the compensating current to both electrodes as just described, and as before the compensating current Ix can comprise one or more net cathodic or anodic pulses provided to the sensing electrodes S+ and S−. Also, and as before, the compensating current can be provided at the pulse width PW computed earlier, and with an amplitude I set by Qdc as computed (i.e., I=Qdc/PW). As noted above, providing this current should reduce Voff to zero, meaning the algorithm 200 would likely not need to iterate (at step 294) to once again provide a compensating current Ix. In other words, the algorithm 200 of FIG. 14B may only involve a single coarse adjustment to the DC offset Voff at steps 230 or 235, without a need to iterate further.

That being said, the algorithm 200 can iterate as necessary (at step 294). Although not shown, the algorithm 200 could during such iterations provide fine adjustments to Voff as discussed earlier. For example, minimum amounts of charge (Qdc(min)) can be used to provide a fine-adjustment compensating current Ix after the coarse adjustment in FIG. 14B, as discussed with respect to FIG. 11. Alternatively, the DC offset compensation circuitry 150 can be used to provide Idc as a fine adjustment after a coarse adjustment in FIG. 14B, as discussed with respect to FIG. 12. Further to this point, it should be understood that the various examples of DC offset compensation algorithm 200 illustrated herein can be used in different combinations.

Figure 15A:
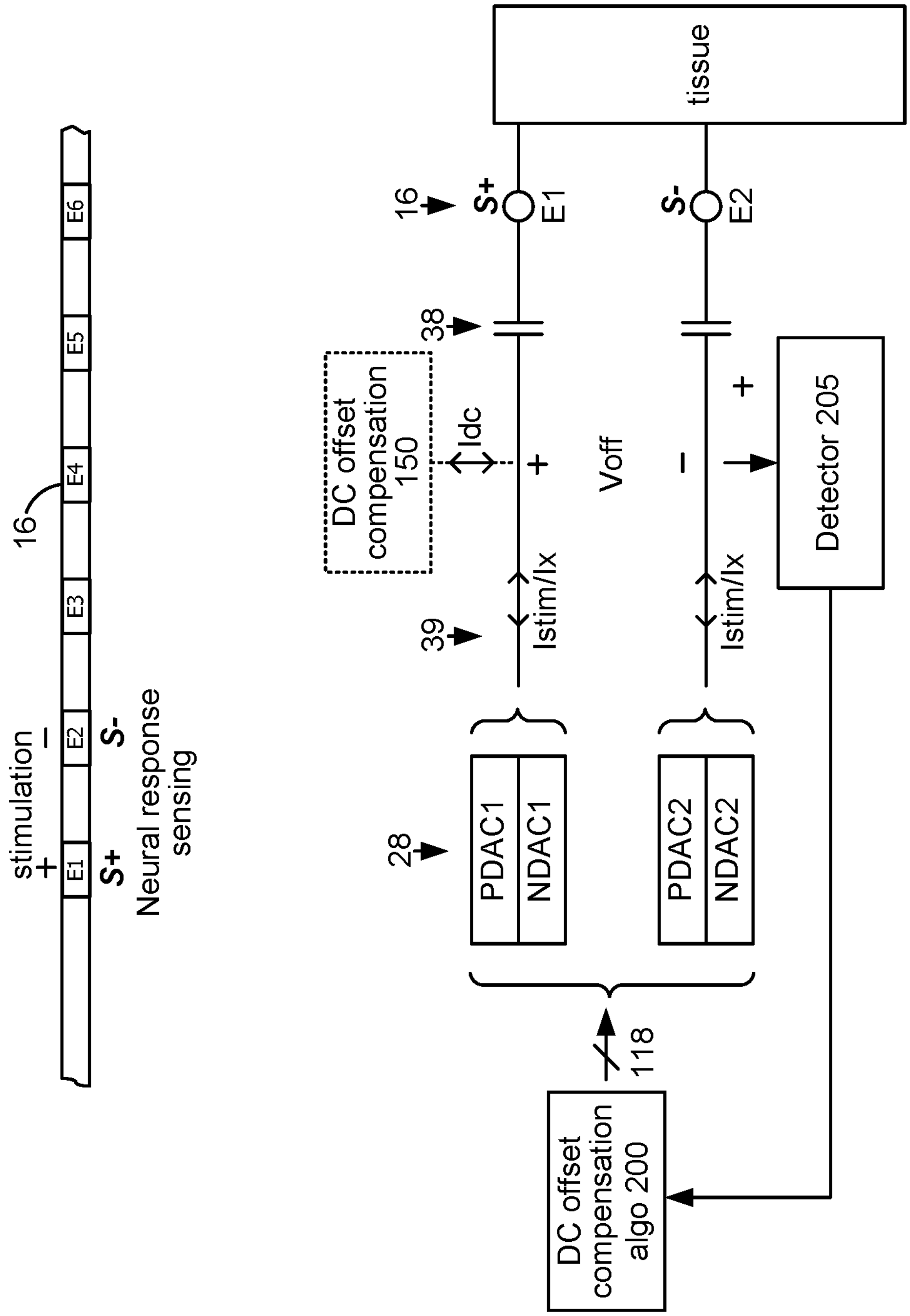
FIGS. 15A-15C show an example in which the DC offset compensation algorithm operates to provide a compensating current by modifying the stimulation current, which is useful when one or more of the sensing electrodes is also used to provide the stimulation current.

Examples to this point have assumed that the sensing electrodes (e.g., S+ and S−) are different from the electrodes used to provide stimulation. However, as noted previously, this is not always the case, and at least one of the sensing electrodes can comprise an electrode that is also used to provide the stimulation. FIG. 15A shows an example in which neural responses are sensed at the same electrodes (e.g., E1 and E2) used to provide stimulation. This can be particular useful when sensing neural responses for particular stimulation therapies, such as Deep Brain Stimulation (DBS).

In this example, the detector 205 and DC offset compensation algorithm 200 can be configured to operate in any of the previously-described ways to provide a compensating current Ix that reduces or eliminates a DC offset voltage (Voff) at the inputs to the sense amp circuitry 110. Thus, in this example, the stimulation circuitry 28 (i.e., P/NDAC1 and P/NDAC2) are controlled both to provide the stimulation current (Istim) and a compensating current (Ix) at the selected electrodes.

The stimulation current Istim and compensating current Ix can be provided at different times. Thus, when it is desired to sense a neural response, the DC offset compensating algorithm 200 can cause the stimulation circuitry 28 to temporarily cease the production of stimulation pulses comprising Istim. The algorithm 200 can then cause the detector 205 to sense whether a DC offset Voff is present at the inputs to the sense amp 110, and cause the stimulation circuitry 28 to provide a compensating current Ix to reduce or eliminate this offset. This can occur in any of the ways described previously. Once the DC offset has been removed, the algorithm 200 can again allow the stimulation circuitry 28 to restart Istim, and sense neural responses in response. Although not shown in FIG. 15A, note that the one or more charge imbalanced pulses comprising the compensating current Ix may differ (e.g., in amplitude, frequency, pulse width, etc.) from the stimulation pulses comprising the stimulation current Istim.

Figure 15B:
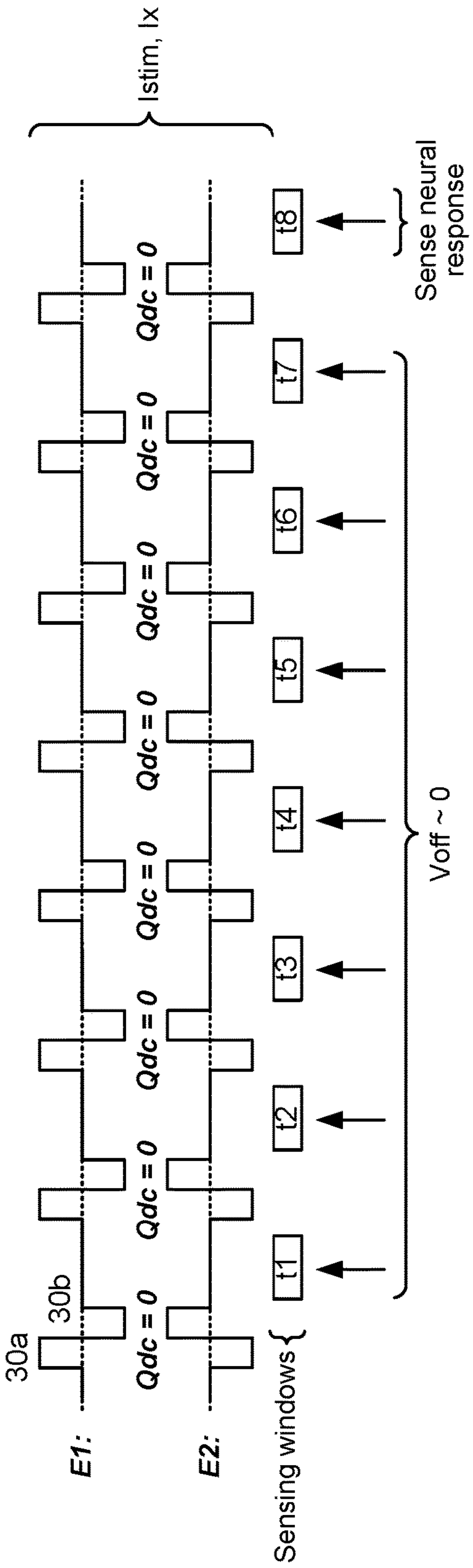
Figure 15C:
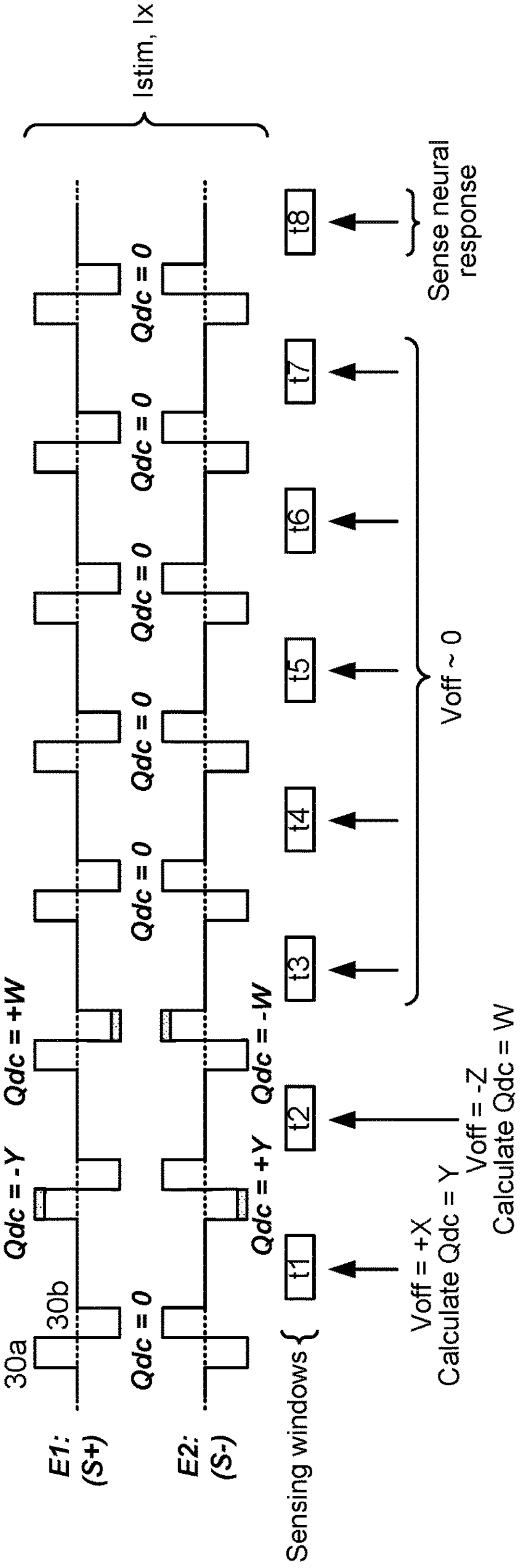

However, the stimulation pulses comprising Istim may themselves be adjusted (charge imbalanced) to provide the compensating current Ix, and this example is shown in FIGS. 15B and 15C. In these figures, it is desired to sense a neural response during a sensing window at time t8 (after one of the stimulation pulses Istim). In preparation for this, the DC offset compensation algorithm 200 will operate to measure the DC offset Voff, and to issue a compensating current Ix if necessary, with Ix comprising an adjustment to Istim. Thus, in FIG. 15B, Voff is determined in preceding sensing windows t1-t7. Because in this example it is assumed that Voff is zero during these sensing windows (or close enough to zero that saturation has not occurred or is not at risk), the pulses comprising Istim are not modified by the algorithm 200. That is, no compensating current Ix is needed, and the Istim pulses continue to be charge balanced, with a net charge Qdc equal to zero, in preparation for neural response sensing during sensing window t8.

FIG. 15C assumes that a significant DC offset Voff is present that requires equilibration, and hence the algorithm 200 operates to modify the Istim pulses to provide a compensating current Ix to remove the offset. During sensing window t1, the algorithm 200 detects a significant DC offset Vofft equal to +X, meaning that high saturation is present or at risk. Thus, a next Istim pulse is adjusted (charge imbalanced) to compensate. Consistent with earlier examples, a net cathodic pulse is issued at S+ (E1) and/or a net anodic pulse is issued at S− (E2) to decrease Voff closer to zero. This can occur in different ways as described earlier, but in this example it is assumed that a net charge Qdc is calculated (Y) using Voff (X). See FIGS. 14A and 14B. This charge imbalance manifests by changing the amplitude of one of the phases 30*a* or 30*b* of this next Istim pulse, although as mentioned previously charging imbalance can be affected in different ways such as by adjusting the pulse width of one of the phases, etc. See FIG. 9B.

Thereafter, the algorithm 200 will again determine the DC offset during sensing window t2. Here is assumed that the DC offset is negative (−Z), meaning in this example that over-compensation occurred earlier, and thus low saturation is present or at risk. Thus, a next Istim pulse is adjusted (charge imbalanced) to compensate. Consistent with earlier examples, a net anodic pulse is issued at S+(E1) and/or a net cathodic pulse is issued at S− (E2) to increase Voff closer to zero. As before, a net charge Qdc (W) is calculated using Voff=−Z to set the charge imbalance of the next Istim pulse. Thereafter, it is assumed during subsequent sensing windows t3-t7 that the DC offset Voff is negligible, and that compensation is not required. Thus, non-adjusted charge-balanced pulses are issued for Istim (Qdc=0), and eventually the neural response is sensed at sensing window t8.

The various algorithms (e.g., 124, 200) and methods more generally disclosed herein can comprise instructions fixed in a computer readable medium, such as a solid-state memory (e.g., control circuitry 102), optical or magnetic disk, and the like. These media may be within the IPG 100, or stored on external systems in manner downloadable to the IPG, such as on various Internet servers and the like.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A stimulator device, comprising:

a plurality of electrode nodes, wherein each of the electrode nodes is associated with a different electrode configured to contact a patient's tissue;

stimulation circuitry configurable to provide stimulation to one or more of the plurality of electrode nodes to provide stimulation to the patient's tissue;

sense amplifier circuitry comprising a first input and a second input, wherein the sense amplifier circuitry is configurable to receive one of the plurality of electrode nodes at the first input, wherein the sense amplifier circuitry is configured to sense a tissue signal;

a detector configured to produce data indicative of the DC offset voltage between the first input and the second input; and control circuitry configured to use the data to control the stimulation circuitry to issue a compensating current at the first input, the second input, or both of the first and second inputs, to reduce or eliminate the DC offset voltage.

2. The stimulator device of claim 1, further comprising a DC-blocking capacitor between each of the electrode nodes and its associated electrode.

3. The stimulator device of claim 2, wherein the compensating current reduces or eliminates the DC offset voltage by charging or discharging the DC-blocking capacitor associated with the first input.

4. The stimulator device of claim 1, wherein the one electrode node received at the first input is different from the one or more electrode nodes that provide the stimulation to the patient's tissue.

5. The stimulator device of claim 1, wherein the sense amplifier circuitry is configured to sense a neural response to the stimulation as the tissue signal.

6. The stimulator device of claim 1, wherein the sense amplifier circuitry is configurable to receive another one of the plurality of electrode nodes at the second input.

7. The stimulator device of claim 6, wherein the control circuitry is configured to issue the compensating current at the first and second inputs to reduce or eliminate the DC offset voltage.

8. The stimulator device of claim 7, wherein the compensating currents at the first and second inputs are of opposite polarities.

9. The stimulator device of claim 6, wherein the electrode nodes received at the first and second inputs are different from the one or more electrode nodes that provide the stimulation to the patient's tissue.

10. The stimulator device of claim 1, wherein the compensating current comprises one or more charge imbalanced pulses.

11. The stimulator device of claim 1, wherein the control circuitry comprises an algorithm to control the stimulation circuitry to issue the compensating current.

12. The stimulator device of claim 11, wherein the algorithm is configured to iterate by periodically producing the data indicative of the DC offset voltage, and periodically using the data to control the stimulation circuitry to issue the compensating current.

13. The stimulator device of claim 12, wherein a charge of the compensating current is adjusted as the algorithm iterates.

14. The stimulator device of claim 11, wherein the algorithm is configured to calculate a charge using the data that eliminates the DC offset voltage, and to control the stimulation circuitry to issue the compensating current with the calculated charge.

15. The stimulator device of claim 11, further comprising DC offset compensating circuitry configured to issue a DC current, wherein the algorithm is further configured to enable the DC offset compensation circuitry to issue the DC current at the first input or the second input to reduce or eliminate the DC offset voltage.

16. The stimulator device of claim 1, wherein the detector comprises an Analog-to-Digital Converter (ADC), wherein the ADC provides a digitized value indicative of the DC offset voltage as the data.

17. The stimulator device of claim 1, further comprising an ADC configured to produce a digitized waveform of the sensed tissue signal, wherein the digitized waveform comprises a plurality of samples.

18. The stimulator device of claim 17, wherein the detector is configured to determine whether the digitized waveform is saturated.

19. The stimulator device of claim 18, wherein the data indicative of the DC offset voltage comprises an indication of high saturation or low saturation.

20. The stimulator device of claim 1, wherein the data comprises one or more digital signals indicative of saturation.

* * * * *